US 6,852,907 B1

(12) United States Patent
Padidam et al.

(10) Patent No.: US 6,852,907 B1
(45) Date of Patent: Feb. 8, 2005

(54) RESISTANCE IN PLANTS TO INFECTION BY SSDNA VIRUS USING INOVIRIDAE VIRUS SSDNA-BINDING PROTEIN, COMPOSITIONS AND METHODS OF USE

(75) Inventors: Malla Padidam, Lansdale, PA (US); Roger N. Beachy, St. Louis, MO (US); Claude M. Fauquet, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/622,500

(22) PCT Filed: Mar. 3, 1999

(86) PCT No.: PCT/US99/04716

§ 371 (c)(1),
(2), (4) Date: Aug. 17, 2000

(87) PCT Pub. No.: WO99/45101

PCT Pub. Date: Sep. 10, 1999

Related U.S. Application Data

(60) Provisional application No. 60/076,627, filed on Mar. 3, 1998.

(51) Int. Cl.[7] .................... C12N 15/82; C12N 15/00; A01H 1/00; C07H 21/04; C12P 21/06

(52) U.S. Cl. ................... 800/280; 800/278; 800/279; 800/288; 800/295; 800/298; 800/301; 536/23.72; 435/69.1; 435/320.1; 435/410; 435/418; 435/419; 435/468

(58) Field of Search .................... 435/69.1, 320.1, 435/410, 418, 419, 468; 536/23, 72; 800/278, 279, 280, 288, 295, 298, 301

(56) References Cited

PUBLICATIONS (Plant Virology, Matthews, R.E.F. 3rd Ed., 1991, Academic Press, San Diego, Calif, p. 424.).*
Padidam, et al., A phage single–stranded DNA (ssDNA) binding pro tein complements ssDNA accumulation of a geminivirus and interferes with viral movement, 1999, *J. Virol.*, 73(2):1609–1616.
Padidam, et al., Tomato leaf curl geminivirus from India has a bipartite genome and coat protein is not essential for infectivity, 1995, *J. Gen. Virol.*, 76:25–35.
Horsch, et al., A simple and general method for transferring genes into plants, 1985, *Science*, 227:1229–1231.
Sanford, et al., Optimizing the biolistic process for different biological applications, 1993, *Meth. Enzymol.*, 217:483–509.
Bates, Electroporation of plant protoplasts and tissues, 1995, *Meth. Cell Biol.*, 50:363–373.
Timmermans, et al., Geminiviruses and their uses as extra–chromosomal replicons, 1994, *Annu. Rev. Physiol. Plant Mol. Biol.*, 45:79–112.

* cited by examiner

Primary Examiner—Elizabeth McElwain
Assistant Examiner—Georgia L Helmer
(74) Attorney, Agent, or Firm—Thomas Fitting; Michael J. McCarthy

(57) ABSTRACT

The invention describes methods for producing plant resistance to a ssDNA virus, particularly a geminivirus such as mastrevirus, curtovirus or begomovirus. The method comprises introducing a ssDNA-binding protein of the *Inoviridae* virus into the plant, and includes a phage coat protein, particularly, a coliphage gene 5 protein. The invention also describes a transgenic plant comprising a gene that expresses the ssDNA-binding protein and vectors for expressing the protein in plants.

28 Claims, 5 Drawing Sheets

RESISTANCE IN PLANTS TO INFECTION BY SSDNA VIRUS USING INOVIRIDAE VIRUS SSDNA-BINDING PROTEIN, COMPOSITIONS AND METHODS OF USE

This application is a 371 of PCT/US99/04716, filed Mar. 3, 1999, which claims the benefit of U.S. Provisional Application No. 60/076,627, filed Mar. 3, 1998, now abandoned.

This invention was made with government support under Contract No. 2630152-1-3036-00 by the Agency for International Development. The government has certain rights in the invention.

TECHNICAL FIELD

The invention relates methods and compositions for producing plants which are resistant to infection by plant viruses.

BACKGROUND

Geminiviruses are plant pathogens that cause significant yield losses in crop plants in many countries of the world (Briddon et al, "Geminiviridae", p. 158–165. In F. A. Murphy (ed.), *Virus Taxonomy, Sixth Report of International Committee on Taxonomy of Viruses*, Springer-Verlag, Vienna & New York, 1995; Frischmuth et al, *Semin. Virol.*, 4:329–337, 1993; Harrison et al, *Ann. Rev. Phytopathol.*, 23:55–82, 1985; Polston et al, *Plant Dis.*, 81:1358–1369, 1997). Different members are transmitted by whiteflies or leafhoppers (Davies et al, *Genet.*, 5:77–81, 1989; Lazarowitz et al, *Crit. Rev. Plant Sci.*, 11:327–349, 1992). Most of the whitefly-transmitted geminiviruses (WTGs) have bipartite genomes while all the leafhopper-transmitted geminiviruses and some of the WTGs have monopartite genomes. The monopartite genomes (2566–3028 nt) encode proteins required for replication, encapsidation and movement, while in the case of the bipartite viruses the movement functions are encoded by a second genome component of similar size (Davies et al, *Genet.*, 5:77–81, 1989; Ingham et al, *Virology*, 207:191–204, 1995; Timmermans et al, *Annu. Rev. Plant Physiol. Plant Mol. Biol.*, 45:79–112, 1994).

Geminiviruses have circular single-stranded (ss) DNA genomes encapsidated in double icosahedral particles. Geminiviruses replicate via a rolling circle mechanism analogous to replication of bacteriophages with ssDNA genomes. The incoming geminivirus single-stranded (ss) DNA is converted by host enzymes to double-stranded (ds) DNA which in turn serves as a template for transcription of early, replication associated genes on the complementary-sense strand. Replication initiator protein (Rep or AC1) is the only viral protein required for replication. In bipartite geminiviruses, a second protein (AC3) enhances replication. AC2, another early gene product, transactivates expression of the coat protein (CP) gene on the virion-sense strand. While the CP is not required for replication of the virus in protoplasts or plants, mutations in CP lead to dramatic decreases in accumulation of ssDNA in protoplasts or plants without affecting the accumulation of dsDNA. On the other hand, tomato golden mosaic virus CP mutations had no effect on DNA accumulation in plants, but reduced ssDNA accumulation while increasing the dsDNA accumulation in protoplasts. In plants, lack of CP results in a complete loss of infectivity of monopartite viruses but not bipartite viruses.

Coat protein may influence the ratios of ss and dsDNA levels in a passive manner by depleting the ssDNA that is available for conversion to dsDNA through encapsidation, or by modulating ssDNA synthesis, or both. No evidence is available for how CP influences ssDNA accumulation in geminiviruses. In tomato leaf curl virus from New Delhi (ToLCV-NbE, hereafter referred as ToLCV), a geminivirus with bipartite genome, disrupting the synthesis of wild type CP resulted in drastic reduction in ssDNA and a three to five fold increase in dsDNA accumulation in infected protoplasts. Inoculated plants, however, develop severe symptoms and accumulate wild type levels of dsDNA and low levels of ssDNA.

There remains a need to better understand the role of CP in geminivirus replication.

BRIEF SUMMARY OF THE INVENTION

We have now discovered that a heterologous ssDNA binding protein can complement CP function in geminivirus ssDNA accumulation. It is also discovered that ToLCV modified to express the ssDNA binding gene 5 protein (g5p) from *E. coli* phage M13 in place of CP accumulates ssDNA to wild type levels in protoplasts, but fails to move efficiently in plants, providing key insight into the present invention. Exemplary heterologous ssDNA-binding proteins are found in the Inoviridae virus family.

Thus, in one embodiment, the invention describes a method for producing in a plant resistance to a single stranded DNA (ssDNA) virus comprising introducing a ssDNA-binding protein of the Inoviridae virus family into the plant. The Inoviridae family virus ssDNA-binding protein is selected from the group consisting of the *Inovirus* and *Plectrovirus* genuses, and the *Inovirus* genus virus is selected from the group consisting of Coliphage, enterobacteria phage, *Pseudomonas* phage, *Vibrio* phage and *Xanthomonas* phage species. A preferred Coliphage species of virus is selected from the group consisting of AE2, dA, Ec9, f1, fd, HR, M13, ZG/2 and ZJ/2 coliphages, with a coat protein or a gene 5 protein being more preferred. Particularly preferred is the Coliphage M13 gene 5 protein.

The method of introduction of the ssDNA-binding protein into the plant can include producing a transgenic plant containing an expression vector for expressing the protein, contacting a plant with an expression vector for expressing the protein, infecting the plant with a carrier vector, such as an *Agrobacterium* vector, and the like methods.

The invention also describes a DNA expression vector comprising a nucleotide sequence that encodes a ssDNA-binding protein of the Inoviridae virus family, wherein the vector is capable of expressing the protein in plants. The vector is used in the methods described herein.

Also described is a composition for producing resistance to a ssDNA virus that infects plants comprising an effective amount of a DNA expression vector comprising a nucleotide sequence that encodes a ssDNA-binding protein of the Inoviridae virus family, wherein the vector is capable of expressing the protein in the plant. In preferred embodiments, the vector is a carrier vector which can infect the plant. A particularly preferred vector is an *Agrobacterium* vector.

The invention also contemplates a transgenic plant containing a DNA expression vector of this invention, which is resistant to ssDNA virus infection due to the expression of a ssDNA binding protein as described herein.

Other embodiments will be apparent from the teachings of the specification and the claims.

BRIEF DESCRIPTION OF THE DRAWINGS

FIG. 1 illustrates the genome organization and schematic representation of constructs of tomato leaf curl virus from New Delhi (ToLCV-Nde).

FIG. 4 illustrates in vivo binding of gene 5 protein to ToLCV-Nde DNA.

DETAILED DESCRIPTION OF THE INVENTION

Figure 1A:
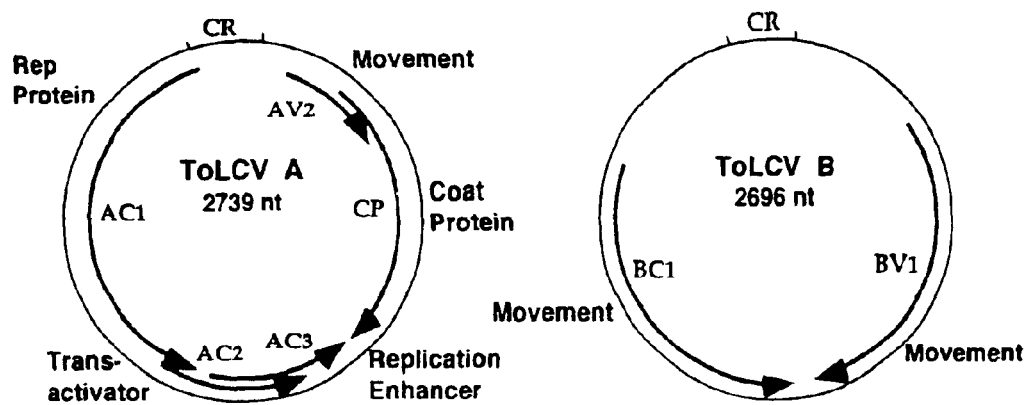
FIG. 1A illustrates the genome organization of ToLCV-Nde showing the ORFs and their functions. CR, common region for both components.

The invention is based on the discovery that ssDNA-binding protein of the Inoviridae family of viruses interferes with virus spread during the infection process of plant viruses of the ssDNA type. By inhibiting virus spread, the virus infection is reduced and/or blocked, thereby increasing plant "resistance" to the virus infection.

The invention describes methods for inhibiting ssDNA plant viruses using Inoviridae family virus ssDNA binding protein, expression vectors capable of expressing the binding protein in plants, compositions for delivery of the expression vectors, and transgenic plants containing genes capable of expressing the binding protein.

A. Methods for Inhibiting ssDNA Plant Viruses

The invention contemplates methods for producing in a plant resistance to infection and/or virulence of a single stranded DNA (ssDNA) virus. The method comprises introducing a ssDNA-binding protein from the Inoviridae family virus into a susceptible plant.

The ssDNA-binding protein is typically provided by expression of a nucleotide sequence which encodes the ssDNA-binding protein and which contains expression control elements which provide for expression of protein in plants.

Introduction of the protein into the plant can be accomplished by a variety of methods including standard gene transfer methods, innoculation of the plant with a transfer or carrier vector (i.e., infection by an engineered plant virus or phage), "biolistic" (i.e., ballistic) introduction of nucleic acids into mature plant tissue, direct DNA uptake into plant protoplast, transformation of plants with *Agrobacterium tumefaciens*-based vectors, and the like well known methods.

Plant expression elements for a nucleotide sequence are generally well known in the art and are not to be considered limiting to the invention. The nucleotide sequence which encodes the ssDNA-binding protein can be present on an expression vector, as a DNA fragment, or as a component of a "transfer" or carrier vector such as the infectious *Agrobacterium* gene transfer system commonly used in plants.

A preferred ssDNA-binding protein is an Inoviridae family virus protein having the ability to bind ssDNA. The preferred protein is either the viral coat protein or the viral "gene 5" protein. Although whole (i.e., native) protein can be used, portions of the whole protein can also be used that contain the ssDNA binding portion of the protein. In addition, it is understood that modifications to the amino acid residue sequence of a native protein can be made without compromising the essential functional properties of the protein according to the invention. Thus, the term "ssDNA-binding protein" means any of a variety of configuration of protein including active fragments, fusion proteins containing an active fragment, whole protein, and derivatives thereof which possess the ssDNA binding activity.

The ability to bind ssDNA can be readily measured by art-recognized procedures, including the binding methods described herein. Thus, the invention is not to be construed as so limited so long as the ssDNA-binding protein has the ability to bind plant viral ssDNA as described herein, and inhibit virus replication and/or viral pathogenesis.

The Inoviridae family of viruses is a large family that includes the *Inovirus* and *Plectrovirus* genera. Preferred *Inovirus* species include Coliphage, enterobacteria phage, *Pseudomonas* phage, *Vibrio* phage and *Xanthomonas* phage species. Preferred Coliphage species include AE2, dA, Ec9, f1, fd, HR, M13, ZG/2 and ZJ/2 coliphages. A particularly preferred protein is the Coliphage M13 gene 5 protein.

In preferred embodiments, the Coliphage M13 gene 5 protein has the amino acid residue sequence shown in SEQ ID NO 1.

In a related embodiment, the method comprises introducing the ssDNA-binding protein by preparing a transgenic plant which comprises a gene capable of expressing the protein, and thereby providing plant resistance to the ssDNA plant virus. The methods for preparing a transgenic plant capable of expressing an foreign protein such as the ssDNA-binding protein of this invention are described further herein.

In a further related embodiment, the methods comprises introducing the ssDNA-binding protein by contacting the plant with a composition containing an expression vector capable of expressing the protein in the plant. Methods for preparing and using an expression vector in a composition according to the invention are described further herein.

In the various nucleic acid-based methods in which a nucleotide sequence encodes the ssDNA-binding protein and is capable of expressing the protein, it is understood that the nucleotide sequence can vary in content so long a contemplated ssDNA-binding protein is encoded. For example, the genetic code tolerates variation in codon usage for encoding an amino acid residue sequence, and therefore the invention is not to be construed as limited to a particular nucleotide sequence. However, it is also understood that an expression environment, e.g., the plant cell, has codon usage preferences, and therefore it is desirable to utilize the preferred codons to optimize expression of expressible genes in plants.

In this regard, a preferred nucleotide sequence for use in an expression vector or transgenic plant of this invention can utilize preferred codons. A particularly preferred nucleotide sequence for use in the present invention encodes an M13 gene 5 protein, preferably the amino acid residue sequence shown in SEQ ID NO 1. In one embodiment, a preferred nucleotide sequence comprises the nucleotide sequence shown in SEQ ID NO 2 which is the native nucleotide sequence from the M13 viral genome encoding the native M13 gene 5 protein. In another embodiment, a preferred nucleotide sequence comprises the nucleotide sequence shown in SEQ ID NO 3 which is a synthetic nucleotide sequence designed to incorporate preferred codon usages for highly expressed human genes, and which encodes the native M13 gene 5 protein.

The complete sequence of bacteriophage M13, including the gene 5 coding sequence, is available from GenBank as Accession numbers V00604, J02461 and M10377. The amino acid residue sequence and nucleotide sequence encoding M13 gene 5 is shown in SEQ ID Nos 1 and 2, respectively.

The introduced protein is effective at inhibiting infection of any ssDNA virus that infects plants. Preferred viruses are the Geminiviridae family of viruses, which includes *Mastrevirus, Curtovirus* and *Begomovirus* genera.

Preferred *Mastrevirus* genus species are selected from the group consisting of *Bajra* streak virus, Bean yellow dwarf virus, *Bromus* striate mosaic virus, Chickpea chlorotic dwarf virus, Chloris striate mosaic virus, *Digitaria* streak virus, *Digitaria* striate mosaic virus, Maize streak virus//Ethiopia, Maize streak virus//Ghanal, Maize streak virus//Ghana2, Maize streak virus//Kenya, Maize streak virus//Komatipoort, Maize streak virus//Malawi, Maize streak virus//Mauritius, Maize streak virus//Mozambique, Maize streak virus//Nigeria1, Maize streak virus//Nigeria2, Maize streak virus//Nigeria3, Maize streak virus//Port Elizabeth, Maize streak virus//Reunion1, Maize streak virus//Reunion2, Maize streak virus//*Setaria*, Maize streak virus//South Africa, Maize streak virus//Tas, Maize streak virus//Uganda, Maize streak virus//Vaalhart maize, Maize streak virus//Vaalhart wheat, Maize streak virus//Wheat-eleusian, Maize streak virus//Zaire, Maize streak virus//Zimbabwe1, Maize streak virus//Zimbabwe2, Miscanthus streak virus, *Panicum* streak virus/Karino, *Panicum* streak virus/Kenya, *Paspalum* striate mosaic virus, Sugarcane streak virus//Egypt, Sugarcane streak virus/Natal, Sugarcane streak virus/Mauritius, Tobacco yellow dwarf virus, Wheat dwarf virus/Czech Republic [Wheat dwarf virus-CJI, WDV-CJI], Wheat dwarf virus/France and Wheat dwarf virus/Sweden.

Preferred *Curtovirus* genus species are selected from the group consisting of Beet curly top virus-California, Beet curly top virus-California//Logan, Beet curly top virus-CFH, Beet curly top virus//Iran, Beet curly top virus-Worland, Horseradish curly top virus, Tomato leafroll virus and Tomato pseudo-curly top virus.

Preferred *Begomovirus* genus species are selected from the group consisting of *Abutilon* mosaic virus, *Acalypha* yellow mosaic virus, African cassava mosaic virus//Ghana, African cassaya mosaic virus/Kenya, African cassaya mosaic virus/Nigeria, African cassaya mosaic virus/Uganda, *Ageratum* yellow vein virus, *Althea rosea* enation virus, *Asystasia* golden mosaic virus, Bean calico mosaic virus, Bean dwarf mosaic virus, Bean golden mosaic virus-Brazil, Bean golden mosaic virus-Puerto Rico, Bean golden mosaic virus-Puerto Rico/Dominican Rep. [Bean golden mosaic virus-Dominican Rep., BGMV-DR], Bean golden mosaic virus-Puerto Rico/Guatemala [Bean golden mosaic virus-Guatemala, BGMV-GA], Bhendi yellow vein mosaic virus, Chino del tomate virus [Tomato leaf crumple virus, TLCrV], Cotton leaf crumple virus, Cotton leaf curl virus-India, Cotton leaf curl virus-Pakistan1/Faisalabad1 [Cotton leaf curl virus-Pakistan2], Cotton leaf curl virus-Pakistan1/Faisalabad2 [Cotton leaf curl virus-Pakistan3], Cotton leaf curl virus-Pakistan1/Multan [Cotton leaf curl virus-Pakistan1], Cotton leaf curl virus-Pakistan2/Faisalabad [Pakistani cotton leaf curl virus], Cowpea golden mosaic virus, *Croton* yellow vein mosaic virus//Lucknow, *Dolichos* yellow mosaic virus, East african cassaya mosaic virus/Kenya, East african cassaya mosaic virus/Malawi, East african cassaya mosaic virus/Tanzania, East african cassaya mosaic virus/Uganda//1 [African cassaya mosaic virus-Uganda variant], East african cassaya mosaic virus/Uganda//2, Eclipta yellow vein virus, Eggplant yellow mosaic virus, *Eupatorium* yellow vein virus, *Euphorbia* mosaic virus, Honeysuckle yellow vein mosaic virus, Horsegram yellow mosaic virus, Indian cassaya mosaic virus, *Jatropha* mosaic virus, *Leonurus* mosaic virus, Limabean golden mosaic virus, Lupin leaf curl virus, Macroptilium golden mosaic virus-Jamaica//2, Macroptilium golden mosaic virus-Jamaica//3, *Macrotyloma* mosaic virus, Malvaceous chlorosis virus, Melon leaf curl virus, Mungbean yellow mosaic virus, Okra leaf curl virus//Ivory Coast, Okra leaf curl virus//India, Papaya leaf curl virus, Pepper huasteco virus, Pepper golden mosaic virus, [Texas pepper virus], Pepper mild tigrA virus, Potato yellow mosaic virus//Guadeloupe, Potato yellow mosaic virus/Trinidad and Tobago, Potato yellow mosaic virus/Venezuela, Pseuderanthemum yellow vein virus, *Rhynchosia* mosaic virus, Serrano golden mosaic virus, *Sida* golden mosaic virus/Costa Rica, *Sida* golden mosaic virus/Honduras, *Sida* golden mosaic virus/Honduras//Yellow vein, *Sida* yellow vein virus, *Solanum* apical leaf curl virus, Soybean crinkle leaf virus, Squash leaf curl virus, Squash leaf curl virus/Extended host, Squash leaf curl virus/Restricted host, Squash leaf curl virus/Los Mochis, Squash leaf curl virus-China, Tomato golden mosaic virus/Common strain, Tomato golden mosaic virus/ Yellow vein strain, Tobacco leaf curl virus//India, Tobacco leaf curl virus-China, Tomato leaf curl virus//*Solanum* species D1, Tomato leaf curl virus//*Solanum* species D2, Tomato leaf curl virus-Australia, Tomato leaf curl virus-Bangalore1 [Indian tomato leaf curl virus-BangaloreI], Tomato leaf curl virus-Bangalore2, [Indian tomato leaf curl virus, ItoLCV], Tomato leaf curl virus-Bangalore3 [Indian tomato leaf curl virus-BangaloreII], Tomato leaf curl virus-New Delhi/Severe [Tomato leaf curl virus-India2, ToLCV-IN1], Tomato leaf curl virus-New Delhi/Mild [Tomato leaf curl virus-India2, ToLCV-IN2], Tomato leaf curl virus-New Delhi/Lucknow [Indian tomato leaf curl virus], Tomato leaf curl virus//Senegal, Tomato leaf curl virus-Sinaloa [Sinaloa tomato leaf curl virus, STLCV], Tomato leaf curl virus-Taiwan, Tomato leaf curl virus-Tanzania, Tomato mottle virus, Tomato mottle virus-Taino [Taino tomato mottle virus, TTMoV], Tomato severe leaf curl virus//Guatemala, Tomato severe leaf curl virus//Honduras, Tomato severe leaf curl virus//Nicaragua, Tomato yellow dwarf virus, Tomato yellow leaf curl virus-China, Tomato yellow leaf curl virus-Israel, Tomato yellow leaf curl virus-Israel/Mild, Tomato yellow leaf curl virus-Israel/Egypt, [Tomato yellow leaf curl virus-Egypt, TYLCV-EG], Tomato yellow leaf curl virus-Israel//Cuba, Tomato yellow leaf curl virus-Israel//Jamaica, Tomato yellow leaf curl virus-Israel//Saudi Arabia1, [Tomato yellow leaf curl virus-Northern Saudi Arabia, TYLCV-NSA], Tomato yellow leaf curl virus-Nigeria, Tomato yellow leaf curl virus-Sardinia, Tomato yellow leaf curl, virus-Sardinia/Sicily [Tomato yellow leaf curl virus-Sicily, TYLCV-SY], Tomato yellow leaf curl virus-Sardinia/ Spain//1[Tomato yellow leaf curl virus-Spain, TYLCV-Sp], Tomato yellow leaf curl virus-Sardinia/Spain//2 [Tomato yellow leaf curl virus-Almeria, TYLCV-Almeria], Tomato yellow leaf curl virus-Sardinia/Spain//3 [Tomato yellow leaf curl virus-European strain], Tomato yellow leaf curl virus-Saudi Arabia [Tomato yellow leaf curl virus-Southern Saudi Arabia, TYLCV-SSA], Tomato yellow leaf curl virus-Tanzania, Tomato yellow leaf curl virus-Thailand//1, Tomato yellow leaf curl virus-Thailand//2, Tomato yellow leaf curl virus//Yemen, Tomato yellow mosaic virus-Brazil// 1, Tomato yellow mosaic virus-Brazil//2, Tomato yellow mottle virus, Tomato yellow vein streak virus-Brazil, Watermelon chlorotic stunt virus, Watermelon curly mottle virus and Wissadula golden mosaic virus-Jamaica//1.

Other ssDNA plant viruses include Banana bunchy top virus, Coconut foliar decay virus, Fababean necrotic yellows virus, Milk vetch dwarf virus and Subterranean clover stunt virus.

The above described ssDNA plant viruses which can be inhibited by the present methods infect a large number of plant species. Insofar as new plant species can be discovered which are susceptible to infection by a ssDNA plant virus described according to the present invention, it is to be understood that the invention is not intended to be so limited to known plants. Instead, a plant according to the present methods is intended to be any plant which is susceptible to infection by the described ssDNA plant virus, which susceptibility can be readily determined by art recognized methods, including the infection procedures described herein.

The term "plant" includes whole plants, plant organs (e.g., leaves, stems, roots, etc.), seeds and plant cells and progeny of same. The class of plants which can be used in the method of the invention is generally as broad as the class of higher plants amenable to transformation techniques, including both monocotyledonous (monocots) and dicotyledonous (dicots) plants. It includes plants of a variety of ploidy levels, including polyploid, diploid and haploid.

Exemplary plants which are susceptible to infection, and therefore are targets for the treatment methods and compositions described herein include, but are not limited to, a plant is selected from the group consisting of *Abutilon, Acalypha*, apple, *Ageratum, Althea rosea, Asystasia*, Bajra, banana, barley, beans, beet, Blackgram, *Bromus*, Cassaya, chickpea, Chilllies, *Chloris*, clover, coconut, coffee, cotton, cowpea, *Croton*, cucumber, *Digitaria, Dolichos*, eggplant, *Eupatorium, Euphorbia*, fababean, honeysuckle, horsegram, *Jatropha, Leonurus*, limabean, Lupin, Macroptilium, *Macrotyloma*, maize, melon, millet, mungbean, oat, okra, *Panicum*, papaya, *Paspalum*, peanut, pea, pepper, pigeon pea, pineapple, *Phaseolus*, potato, Pseuderanthemum, pumpkin, *Rhynchosia*, rice, Serrano, *Sida*, sorghum., soybean, squash, sugarcane, sugarbeet, sunflower, sweet potato, tea, tomato, tobacco, watermelon, wheat and Wissadula, or any individual plant or combination of plants thereof.

Preferred examples of the methods of the invention are described herein using the M13 gene 5 protein expressed using a recombinant tomato leaf curl virus (ToLCV) vector on tobacco plants and protoplasts. The ToLCV viral genomic nucleotide sequences for both the A and B components of the ToLCV bipartite genome are known, and are available as GenBank Accession numbers U15015 and U15016, respectively, and are shown in SEQ ID NOs 4 and 5, respectively.

B. Nucleic Acid Molecules

The invention also contemplates a nucleic acid molecule, such as a DNA expression vector, useful for expression of a ssDNA-binding protein of this invention in plants. Thus the nucleic acid molecule contains a nucleotide sequence which encodes the ssDNA-binding protein of this invention and further contains elements for regulation and control of gene expression in plants. Exemplary elements for expression in plants are described in U.S. Pat. Nos. 5,188,642, 5,202,422, 5,463,175 and 5,639,947, the disclosures of which are hereby incorporated by reference. In addition, the methods of manipulating nucleic acids and the production of expression vectors for use in plants is generally well known and therefore not to be construed as limiting to the present invention.

Exemplary expression vectors and systems for introduction of a ssDNA-binding protein into plants are described in the Examples.

Thus, in one embodiment, the invention describes a nucleic acid-based expression system comprising a nucleotide sequence that encodes a ssDNA-binding protein of the Inoviridae virus family, where the expression system is capable of expressing the protein in a plant susceptible to infection by a ssDNA plant virus as described herein.

The sSDNA-binding protein can be any protein as described herein and as is preferred in practicing the methods for the invention. Particularly preferred is the M13 gene 5 protein, such as the amino acid residue sequence shown in SEQ ID NO 1.

The expression system can be a vector or a gene, depending upon the contemplated usage. In the case of a transgenic plant, the invention describes a gene comprising a nucleotide sequence which defines an expression cassette, i.e., the necessary elements for expression of a ssDNA-binding protein structural gene including promoters, transcription start signals, translation start signals, the structural protein coding sequence, and translation and transcription stop sequences, as are well known. In the case of a vector or infectious agent used to introduce an expression cassette, the vector or agent comprises additional genetic elements suitable for the vector or infectious agent's function.

For example, the vector may also contain elements which provide for replication, manipulation and the like, such as in found on plasmids which facilitate bulk preparation of the vector. In the case of infectious agents, which are typically modified plant viruses or plant phage which can infect the plant, the agent may contain additional elements for replication of the agent and assembly into an infectious particle, as are well known.

A preferred expression cassette in a vector, gene or infectious agent according to the invention comprises a nucleotide sequence shown in SEQ ID NOs 2 or 3 as described herein.

For general cloning of nucleic acids, plasmids are used as are well known. A preferred cloning plasmid used herein is the pBluescript II SK vector (Stratagene, La Jolla, Calif.). The complete nucleotide sequence of the pBluescript plasmid is available in GenBank as Accession number X52330, and is also shown in SEQ ID NO 6.

For plant transformations, a variety of methods, vectors and agents are available, and therefore the invention is not to be construed as so limited. Exemplary methods include plant transformation, comprising direct uptake of an expression cassette nucleic acid(s) into a protoplast followed by plant regeneration to form a plant, electroporation into a protoplast, biolistic delivery of nucleic acid into either cultured plant cells or whole plant tissue, pollen-mediated transformations, infection by a recombinant virus or phage agent, such as the modified ToLCV or an *Agrobacterium*-mediated transformation, and the like. Exemplary vectors for conducting some of the above methods include pBIN19 (Bevan et al, *Nucl. Acids Res.*, 12:8711, 1984; GenBank Accession number U09365), pMON316 or pMON available from Monsanto (St. Louis, Mo.), pGA482 (An et al, *Plant Physiol.*, 81:86, 1986), pCGN1547 (McBride et al, *Plant Mol. Biol.*, 14:269, 1990), pPZP100 (Ajdukiewicz et al, *Plant Mol. Biol.*, 25:989, 1994, and GenBank Accession number U10456), pMOG410, and the like.

C. Transgenic Plants

The invention further contemplates a transgenic plant containing a nucleotide sequence of this invention for expressing the ssDNA-binding protein. The transgenic plant contains an expression cassette as defined herein as a part of the plant, the cassette having been introduced by transformation of a plant with a vector of this invention.

Methods for producing a transgenic plant useful in the present invention are described in U.S. Pat. Nos. 5,188,642; 5,202,422; 5,234,834; 5,463,175; and 5,639,947, the disclosures of which are hereby incorporated by reference.

Techniques for transforming a wide variety of plant species are also well known and described in the technical and scientific literature. See, for example, Weising et al, *Ann. Rev. Genet.*, 22:421–477, 1988. A constitutive or inducible promoter is operably linked to the desired heterologous DNA sequence encoding a ssDNA-binding protein of this invention in a suitable vector. The vector comprising a promoter fused to the heterologous DNA will typically contain a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorsulfuron or Basta. Such selective marker genes are useful in protocols for the production of transgenic plants.

DNA constructs containing the expression cassette can be introduced into the genome of the desired plant host by a variety of conventional techniques. For example, the DNA construct may be introduced directly into the DNA of the plant cell using techniques such as electroporation and microinjection of plant cell protoplasts. Alternatively, the DNA constructs can be introduced directly to plant tissue using biolistic methods, such as DNA micro-particle bombardment. In addition, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al, *EMBO J.*, 3:2717–2722, 1984. Electroporation techniques are described in Fromm et al, *Proc. Natl. Acad. Sci. USA*, 82:5824, 1985. Biolistic transformation techniques are described in Klein et al, *Nature* 327:70–73, 1987. The full disclosures of all references cited are incorporated herein by reference.

A variation involves high velocity biolistic penetration by small particles with the nucleic acid either within the matrix of small beads or particles, or on the surface (Klein et al, *Nature*, 327:70–73, 1987). Although typically only a single introduction of a new nucleic acid segment is required, this method particularly provides for multiple introductions.

*Agrobacterium tumefaciens*-meditated transformation techniques are well described in the scientific literature. See, for example Horsch et al, *Science*, 233:496–498, 1984, and Fraley et al, *Proc. Natl. Acad. Sci. USA*, 90:4803, 1983. More specifically, a plant cell, an explant, a meristem or a seed is infected with *Agrobacterium tumefaciens* transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al, *Science*, 233:496–498, 1984; Fraley et al, *Proc. Nat'l. Acad. Sci. U.S.A.*, 80:4803, 1983.

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without its transferring ability being affected. By removing the tumor-causing genes so that they no longer interfere, the modified Ti plasmid can then be used as a vector for the transfer of the gene constructs of the invention into an appropriate plant cell, such being a "disabled Ti vector".

All plant cells which can be transformed by *Agrobacterium* and whole plants regenerated from the transformed cells can also be transformed according to the invention so as to produce transformed whole plants which contain the transferred foreign nucleic acid sequence.

There are various ways to transform plant cells with *Agrobacterium*, including:

(1) co-cultivation of *Agrobacterium* with cultured isolated protoplasts, (2) co-cultivation of cells or tissues with *Agrobacterium*, or (3) transformation of seeds, apices or meristems with *Agrobacterium*.

Method (1) requires an established culture system that allows culturing protoplasts and plant regeneration from cultured protoplasts.

Method (2) requires (a) that the plant cells or tissues can be transformed by *Agrobacterium* and (b) that the transformed cells or tissues can be induced to regenerate into whole plants.

Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

The present invention embraces use of the expression vectors described herein in transformation of any plant, including both dicots and monocots. Transformation of dicots is described in references above. Transformation of monocots is known using various techniques including electroporation (e.g., Shimamoto et al, *Nature*, 338:274–276, 1992; ballistics (e.g., European Patent Application 270,356); and *Agrobacterium* (e.g., Bytebier et al, *Proc. Nat'l Acad. Sci. USA*, 84:5345–5349, 1987).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium typically relying on a biocide and/or herbicide marker which has been introduced together with the nucleotide sequences. Plant regeneration from cultured protoplasts is described in Evans et al, Handbook of Plant Cell Culture, pp. 124–176, MacMillan Publishing Company, New York, 1983; and Binding, Regeneration of Plants, Plant Protoplasts, pp. 21–73, CRC Press, Boca Raton, 1985. Regeneration can also be obtained from plant callus, explants, organs, or parts thereof. Such regeneration techniques are described generally by Klee et al, *Ann. Rev. Plant Phys.*, 38:467–486, 1987.

One of skill will recognize that, after an expression cassette is stably incorporated in transgenic plants and confirmed to be operable, it can be introduced into other plants by sexual crossing. Any of a number of standard breeding techniques can be used, depending upon the species to be crossed.

D. Compositions

Also contemplated is a composition useful for introducing a nucleotide sequence of this invention into plants. The composition is useful for producing resistance to a ssDNA virus that infects plants, and comprises an effective amount of the nucleotide sequence according to the invention for introducing the ssDNA-binding protein into a plant, and depends upon the method used for introducing the protein to the plant. For example, using direct DNA uptake by protoplast, the composition is a aqueous solution containing nucleic acid and buffers to facilitate uptake by protoplast, as is well known. For transformation by an *Agrobacterium* vector, the composition contains a suspension of *Agrobacteria* containing the nucleotide sequence capable of expressing the sSDNA-binding protein.

E. Systems for Use

The present invention also contemplates a system, preferably in kit form, useful for practicing the methods of the present invention. Thus, the kits are useful for introducing a nucleic acid sequence of the present invention into a plant as practiced in the methods of this invention.

The kit comprises, in an amount sufficient to perform at least one introduction, a composition of the present invention comprising a nucleic acid molecules which comprise a nucleotide sequence capable of expressing a ssDNA-binding protein according to the present invention, present in a packaging material or container for providing the system.

Instructions for use of the packaged reagent are also typically included in the system in the form of a label or packaging insert.

"Instructions for use" typically include a tangible expression describing the contents of the reagent(s) in the system or at least one method parameter such as the relative amounts of composition and plant to be admixed, procedures for contacting the plant, temperature, buffer conditions and the like for practicing a method of the invention. Typically, the instructions will recite the method for contacting a plant to introduce the ssDNA-binding protein of the invention into a plant, and thereby inhibit symptoms of ssDNA virus infection in the plant.

The reagent species, infectious agent, virus or phage, nucleic acid molecule or expression vector for practicing a method described herein can be provided in solution, as a liquid dispersion or as a substantially dry power, e.g., in lyophilized form.

The term "package" refers to a solid matrix or material such as glass, plastic (e.g., polyethylene, polypropylene and polycarbonate), paper, foil and the like capable of holding within fixed limits a reagent such as a polynucleotide, transformation agent, infectious virus or phage of the present invention. Thus, for example, a package can be a bottle, vial, plastic and plastic-foil laminated envelope or the like container used to contain a contemplated composition.

The package can contain one or more unit dosages of the composition of the invention, or may alternatively be packaged with the composition provided in bulk.

A system of this invention may comprise a carrier means being compartmentalized to receive in close confinement one or more container means such as vials, tubes, and the like, each of the container means comprising one of the separate elements to be used in the method. For example, one of the container means may comprise a composition for infecting a plant. The kit may also have containers containing any other reagents used to practice the methods of the invention.

Other uses will be apparent to one skilled in the art in light of the present disclosures and the examples that follow.

EXAMPLES

The following examples are provided by way of illustration and not limitation.

1. Plasmid Constructs

Figure 1B:
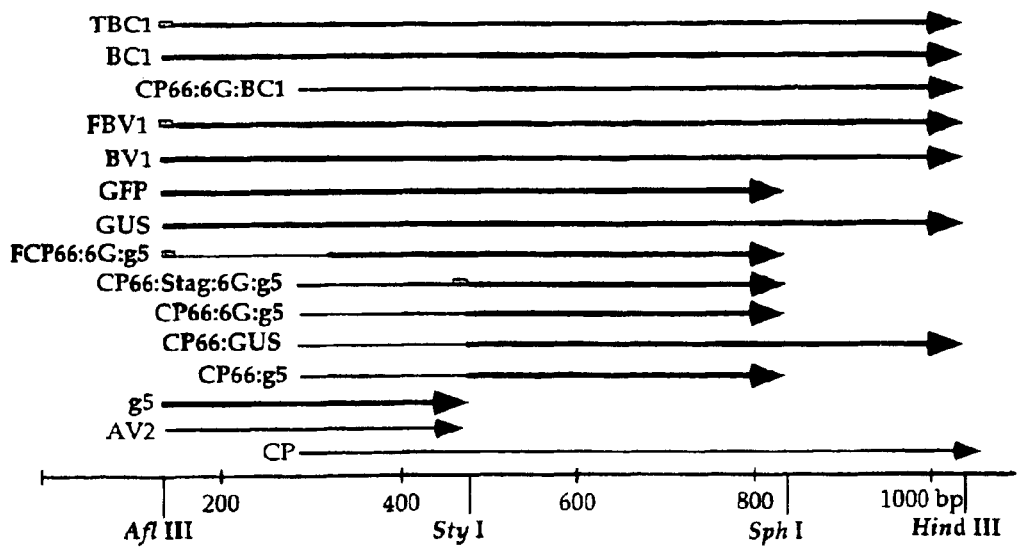
FIG. 1B illustrates a linear physical map of AV2 and CP region of ToLCV-Nde is shown at the bottom with nucleotide positions and relevant restriction enzyme sites. The positions of different gene replacements are shown above the linear map. Note that the gene replacements shown are not to the scale. Descriptions of the constructs are given in Table 1.

Infectious clones of the A and B components of tomato leaf curl virus (Padidam et al, *J. Gen. Virol.*, 76:25–35, 1995) were employed to generate the virus constructs used herein. The genome organization of ToLCV and schematic representation of virus constructs used are shown in FIG. 1 and the detailed descriptions and methods of construction of each of the plasmid are summarized in Table 1. Partial head to tail dimers made from these constructs were used to infect *Nicotiana benthamiana* plants and *N. tabacum* BY2 protoplasts.

TABLE 1

Description and method of construction of viral DNAs

| Construct | Description and method of construction |
|---|---|
| AV2⁻CP⁻ | A double mutant of AV2 and coat protein (CP) in which Met1 codon of AV2 was changed to termination codon and Arg66 codon of CP was frame shifted. The mutant has been described earlier as M1te/R66fr (Padidam et al, Virology, 224:390–404, 1996) |
| g5AV2⁻CP⁻ | A 264-bp sequence coding for gene 5 (g5) protein from bacteriophage M13mp18 vector was amplified by PCR (10 cycles) and cloned between Afl III (nt 125) and Sty I (nt 479) sites resulting in replacement of AV2 ORF and overlapping 5' CP ORF sequences with g5. |
| g5⁻AV2⁻CP⁻ | A negative control of g5AV2⁻CP⁻construct in which Met1 codon of g5 was mutated to a termination codon. |
| CP⁻ | A mutant of CP made by end-filling and religation at the unique Sty I site (nt 479) causing frame shift at Arg66 codon and termination after amino acid (aa) 69. The mutant has been described earlier as R66fr (Padidam et al, Virology, 224:390–404, 1996). |
| CP66:g5 | A 264 bp sequence coding for g5 protein from M13mp18 vector was amplified by PCR (10 cycles) and cloned between and Sty I (nt 479) and Sph I (nt 836) sites resulting in fusion of g5 sequence to Arg66 codon of CP. |
| CP66:6G:g5 | Similar to CP66:g5 except that an oligonucleotide coding for 6 glycines was inserted between codons for Arg66 of CP and Met1 of g5. |
| CP66:g5⁻ | A negative control in which Arg66 codon of CP66:g5 was frame shifted. |
| CP66:Stag:6G:g5 | Similar to CP66:6G:g5 except that a sequence coding for the 15 aa Stag peptide epitope [KETAAAKFERQHMDS (SEQ ID NO:7); (Kim et al, J.S., Protein Sci., 2:348–356, 1993)] was inserted after Arg66 codon of CP. Stag epitope was inserted to immunolocalize the CP66:6G:g5 protein in protoplasts using the S-protein coupled to the FITC. |
| FCP66:6G:g5 | A sequence coding for 9 aa Flag peptide epitope [MDYKDDDDK (SEQ ID NO:8); (Ropp et al, J. Immunol. Methods., 88:1–18, 1986)] was added before the Met1 codon of CP66:6G:g5 and cloned between Afl III (nt 125) and Sph I (nt 836). AV2 ORF is deleted in this construct. Flag epitope was added to immunoprecipitate the CP66:6G:g5 protein from protoplasts using the anti-Flag antibody. |
| CP66:GUS | A 1806-bp DNA fragment coding for β-glucuronidase (GUS) protein (Jefferson et al, Plant Mol. Biol. Rep., 5:387–405, 1987) was PCR amplified (10 cycles) and cloned between Sty I (nt 479) and Hind III (nt 1041) sites of A component. The Hind III site was created at the codon for Tyr251 of CP [15-bp before the termination codon, (Padidam et al, Virology, 224:390–404, 1996)]. This facilitated replacement CP sequence with other sequences. |
| GUSAV2⁻CP⁻ | A 1869-bp Nco I to EcoR I DNA fragment coding for GUS protein was cloned between Afl III (nt 125) and Hind III (nt 1041) sites of A component after blunt ending the EcoR I site on the GUS gene and Hind III site on A component DNA. |
| GFPAV2⁻CP⁻ | A 717-bp with Nco I to BamH I DNA fragment coding for green fluorescent protein [GFP - S65C, M153T, V163A; (Reichel et al, Proc. Natl. Acad. Sci. USA, 93:5855–5893, 1996)] was cloned between Afl III (nt 125) and Sph I (nt 836) sites of A component after blunt ending the BamH I site on the GFP gene and Sph I site on A component DNA. |
| BV1AV2⁻CP⁻ | A 849-bp sequence coding for BV1 from B component of ToLCV was amplified by PCR (10 cycles) and cloned between Afl III (nt 125) and Hind III (nt 1041) sites of A component. |
| FBV1AV2⁻CP⁻ | Similar to BV1AV2⁻CP⁻ except that sequence coding for 9 aa Flag peptide was added before the Met1 codon of BV1. Flag epitope was added to immunolocalize the BV1 protein in protoplasts using the anti-Flag antibody. |
| BC1AV2⁻CP⁻ | A 882-bp sequence coding for BC1 from B component of ToLCV was amplified by PCR (10 cycles) and cloned between Afl III (nt 125) and Hind III (nt 1041) sites of A component. |
| TBC1AV2⁻CP⁻ | Similar to BC1AV2⁻CP⁻ except that sequence coding for 11 aa T7 [MASMTGGQQMG (SEQ ID NO:9); (Krek et al, Cell, 78:161–172, 1994)] epitope was added before the Met1 codon of BC1. T7 tag epitope was added to immunolocalize the BC1 protein in protoplasts using the anti-T7 tag antibody. |
| Cp66:6G:BC1 | A 900-bp sequence coding for 6 glycines and BC1 from B component of ToLCV was amplified by PCR (10 cycles) and cloned between Sty I (nt 479) and Hind III (nt 1041) sites. |
| BC1⁻ | B component DNA in which a frame-shift mutation of BC1 was created by deleting the 3' overhang and religating at the Pst I site (nt 2075) Described earlier as BC1M (Padidam et al, Virology, 224:390–404, 1996) |

2. Protoplast and Plant Inoculations

*N. benthamiana* plants (two week-old seedlings grown in Magenta boxes) and protoplasts isolated from BY2 suspension cells were infected with viral DNAs as described earlier (Padidam et al, *J. Gen. Virol.*, 76:25–35, 1995; Padidam et al, *Virology*, 224:390–404, 1996). Protoplasts were collected from cultures 48 h postinoculation for DNA isolation, immunoprecipitation reactions, and western blot analysis. Plants were scored for symptoms, and the newly formed upper leaves were collected for Southern blot analysis 22 to 25 days following inoculation. To study the local and systemic movement of the virus expressing green fluorescent protein [GFP; Chalfie et al, *Science*, 263:802–805, 1994)], bottom leaves of four-week old seedlings (10 plants per construct) were inoculated. Inoculated and upper non-inoculated leaves were observed at three day intervals for fifteen days under a fluorescence microscope for the detection of fluorescence emitted by GFP. In all experiments that involved plants, wild type B component DNA, which is essential for systemic spread and symptom development, was included.

3. Southern Blotting

Total DNA was isolated from protoplasts (Mettler et al, *Plant Mol. Biol. Rep.*, 5:346–349, 1987) and plants (Dellaporta et al, *Plant Mol. Biol. Rep.*, 1:19–21, 1983) and electrophoresed in 1% agarose gels (without ethidium bromide) and transferred to Hybond nylon membranes (Amersham, Arlington Heights, Ill.) using the standard protocols (Sambrook et al, *Molecular Cloning: A laboratory manual.*, Cold Spring harbor laboratory press. Cold Spring harbor, N.Y., 1989). Hybridization reactions were performed using a randomly primed 32P-labeled A component specific probe (the 900 bp A11 II-Pst I fragment containing ORFs AC1, AC2, and AC3). The amount of viral as and daDNA (super coiled, linear, open circular, and dimeric forms) was quantitated by exposing the Southern blots to storage phosphor screen plates and counting on a PhosphorImager (molecular Dynamics, Sunnyvale, Calif.). The ssDNA form was confirmed by its susceptibility to S1 and mungbean nucleases (Padidam et al, *Virology*, 224:390–404, 1996). In the absence of ethidium bromide, the super coiled viral DNA form runs ahead of the ssDNA form.

4. Immunoprecipitation and Western Blotting

For immunoprecipitation reactions, protoplasts infected with the virus A component expressing CP66:6G:g5 protein tagged with Flag epitope (FCP66:6G:g5, Table 1) were lysed with a hand held polytron in NP40 buffer 50 mM Tris-HCl (pH 7.5), 1% NP40, with 0.15, 0.25, 0.50, 0.75, or 1.0 M NaCl} or RIPA buffer [50 mM Tris-HCl (pH 7.5), 150 mM NaCl, 1% NP40, 0.5% DOC, 0.1% SDS] containing a cocktail of protease inhibitors (Boehringer Mannheim, Indianapolis, Ind.). Cell debris was removed by centrifugation at 4° C. for 10 min at 15,000×g. Lysates were immunoprecipitated with anti-Flag monoclonal M2 antibody covalently linked to agarose (Sigma, St. Louis, Mo.). Immune complexes were washed four times with NP40 or RIPA buffer and once with Tris-buffered saline [50 mM Tris-HCl (pH 7.5), 150 mM NaCl]. Half of each sample was heated in Laemmli sample buffer, fractionated by SDS-PAGE (13% acrylamide), and transferred to PVDF membrane (Schleicher & Schuell, Keene, N.H.). Immunoprecipitated protein was visualized with anti-Flag M2 antibody using ECL-western blot reagents (Pierce, Rockford, Ill.). The remaining half of the immune complex collected by this procedure was used for isolating the viral DNA. Whole cell protein extracts for direct western blotting were prepared by boiling the protoplast pellets with equal volume of 2×Laemmli sample buffer.

5. Immunofluorescence

Protoplasts transfected with viral constructs were cultured on chamber slides (Nalge Nunc, Rochester, N.Y.) for 48 h, fixed with 3% paraformaldehyde in PBSEM [50 mM phosphate (pH 6.95), 150 mM NaCl, 5 mM EGTA, 5 mM MgSO4] for 30 min, and permeabilized with 100% methanol at −20° C. for 10 min. The cells were washed two times with PBSEM containing 0.5% Tween 20 for 30 min. CP66:6G:g5 protein tagged with Stag epitope (CP66:Stag:6G:g5, Table 1) was detected with the S-protein coupled to FITC (Novagen, Madison, Wis.). The fifteen amino acid long Stag peptide was inserted after Arg66 of the CP to construct the CP66:Stag:6G:g5 protein. Flag epitope-tagged BV1, T7 epitope-tagged BC1, CP and β-glucuronidase (GUS) (Table 1) were detected with anti-Flag M2 antibody (Sigma, St. Louis, Mo.), anti-T7 tag antibody (Novagen, Madison, Wis.), anti-CP antisera (Padidam et al, *Virology*, 224:390–404, 1996), and anti-GUS antisera (5'-3', Boulder, Colo.) diluted 1:100 in PBS, respectively. After incubation in primary antibody for 1 h at 30° C., the cells were washed as before and incubated with FITC or rhodamine conjugated IgGs (Pierce, Rockford, Ill.) at a dilution of 1:100. The cells were mounted in Fluoromount G (Electron Microscopy Sciences, Fort Washington, Pa.) and viewed with a Nikon fluorescence microscope or Olympus confocal microscope (for detecting T7 epitope-tagged BC1 protein).

6. ToLCV Expressing Gene 5 Protein or CP66:6G:g5 Protein Accumulates ssDNA to Wild Type Levels in Protoplasts Previous reports work with ToLCV have shown that viral CP and AV2 are not required for virus replication in protoplasts whereas AV2 is required for efficient movement in plants (Padidam et al, *Virology*, 224:390–404, 1996). Coat protein is not essential for systemic movement and symptom development in ToLCV. However, mutations in the CP sequence caused a marked decrease in ssDNA accumulation in *N. bentamiana* and tomato plants and in BY2 protoplasts while increasing dsDNA accumulation in protoplasts. Virus that contained mutations in the AV2 plus CP behaved like AV2 mutants in plants (i.e., poor virus movement and very mild symptoms) and like CP mutants in protoplasts (i.e., decrease in ssDNA and increase in dsDNA accumulation).

Figure 2:
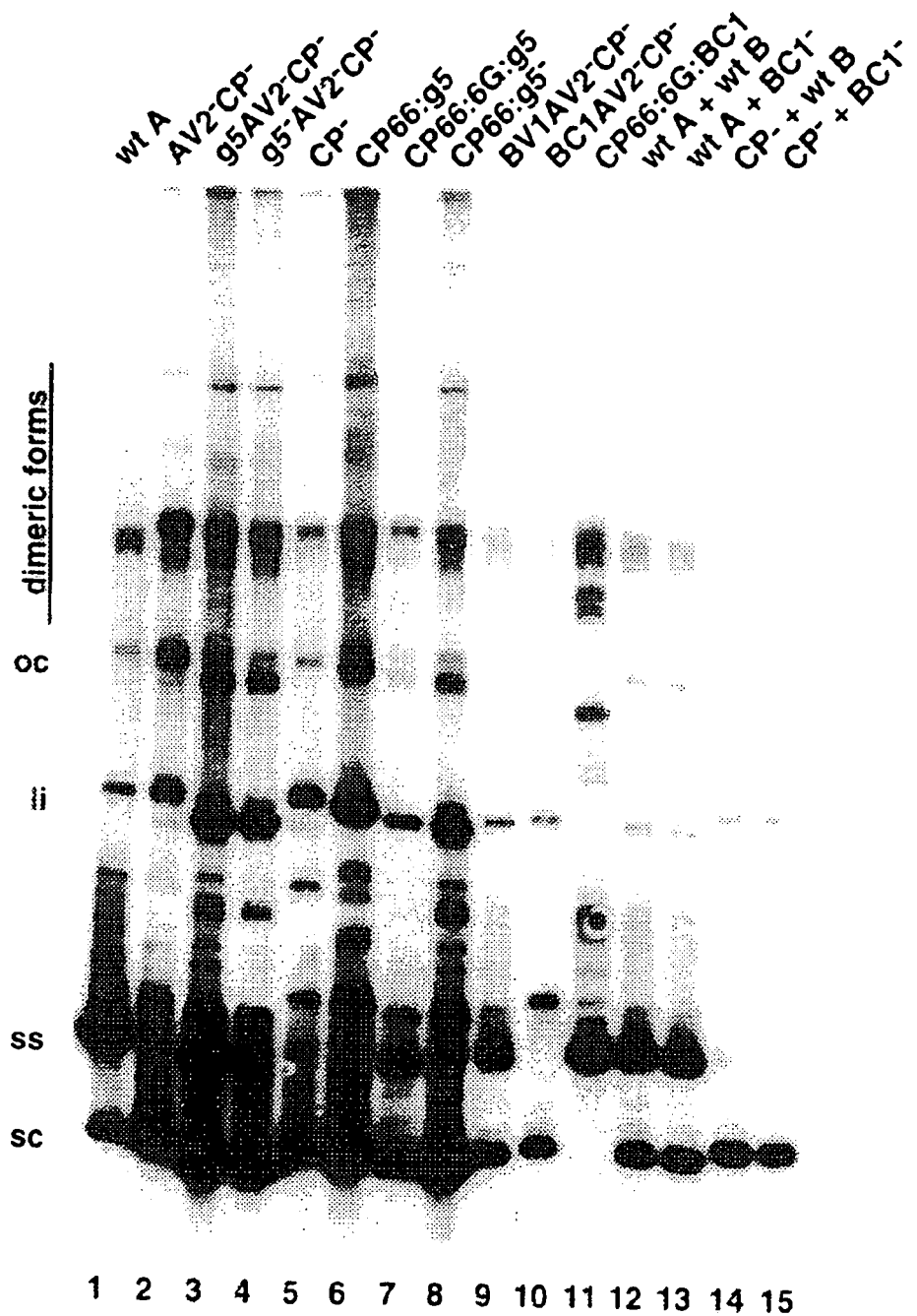
FIG. 2 illustrates replication of ToLCV constructs in infected BY2 protoplasts. Southern blot analysis was performed as described in the Examples. The viral constructs used for infecting protoplasts are shown above the lanes. Protoplasts were inoculated with A component DNA alone (lanes 1–11) or coinoculated with A and B component DNAs (lanes 12–15). Each lane contained 4 µg of DNA prepared from protoplasts (single transfection). Viral DNA was detected using a radioactively-labeled probe from A component DNA. The position of supercoiled (sc), single-stranded (ss), open circular (op), and linear (li) viral DNA forms are indicated. Note that the positions of supercoiled and other viral DNA forms in lane 11 are shifted upwards due to larger size of the CP66:6G:BC1 construct.

The present plasmid constructs provide information on the effects of gene 5 protein (g5p) from *E. coli* phage M13 (Salstrom et al, *J. Mol. Biol.*, 61:489–501, 1971) on replication of ToLCV. Each of these mutations are described in Table 1 and FIG. 1. The AV2 and the overlapping 5' portion of the CP ORF were replaced with the g5p and assayed its effect on virus replication in protoplasts. In these experiments protoplasts were inoculated with wild type (wt) or other mutants, as described below. The modified A component, designated g5AV2⁻CP⁻, led to accumulation of ssDNA to the same levels as did infections with wt virus A component (Table 2; FIG. 2, lanes 1 and 3). However, dsDNA accumulation was high (3 to 6 fold higher than wt levels) and similar to accumulation in virus with mutations in CP (Table 2; FIG. 2, lanes 2–4). Infection by virus in which the g5 gene was mutated to prevent its translation (g5⁻AV2⁻CP, Table 1) behaved like virus infections with A component mutants AV2⁻CP⁻ and CP⁻ (Table 2; FIG. 2, lane 4). Since AV2 is required for efficient virus movement in plants another construct was made in which g5 was fused to CP at Arg66 without affecting the AV2 ORF (CP66:g5, Table 1). CP66:g5 virus A component also led to accumulation of ssDNA, but to lower levels than g5AV2-CP DNA (Table 2; FIG. 2, lane 6). To evaluate whether the N-terminal 66 amino acids (aa) of CP interfered with the ability of g5p to bind DNA, a linker of six glycine residues was introduced between Arg66 of CP and g5 to separate the CP domain from the g5p (CP66:6G:g5). Addition of the linker restored the ability of the CP66:6G:g5 virus A component to accumulate ssDNA to levels comparable to those of g5AV2⁻CP⁻ (Table 2; FIG. 2, lane 7). A control construct in which the g5 portion of the fusion protein was not translated (CP66:g5⁻) failed to accumulate ssDNA (Table 2; FIG. 2, lane 8). The ability of virus A component expressing CP66:6G:g5 protein to accumulate ssDNA was not due to N-terminal 66 aa of the CP was suggested by the facts that the virus A component expressing g5p alone accumulated ssDNA and the virus A components expressing CP66:6G:BC1 (see below) or CP66:6G:AV2 failed to accumulate ssDNA.

TABLE 2

Effect of gene 5 protein on replication and movement of tomato leaf curl virus in *Nicotiana tabacum* protoplasts and *N. benthamiana* plants

Protoplast inoculations

| Virus | ssDNA[a] | dsDNA[a] |
|---|---|---|
| Wild type[c] | 100 | 100 |
| AV2⁻CP⁻ | <1 (0–0.03) | 506 (427–584) |
| g5AV2⁻CP⁻ | 102 (79–133) | 409 (349–573) |
| g5⁻AV2⁻CP⁻ | 7 (5–12) | 384 (210–779) |
| CP⁻ | 5 (2–7) | 241 (148–369) |
| CP66:g5 | 17 (8–27) | 442 (345–576) |
| CP66:6G:g5 | 118 (34–234) | 517 (133–784) |
| CP66:g5⁻ | 9 (3–14) | 424 (179–789) |

Plant inoculations

| Virus | # of plants inoculated | Symptom type | ssDNA[b] | dsDNA[b] |
|---|---|---|---|---|
| Wild type[c] | 20 | Severe | 100 | 100 |
| AV2⁻CP⁻ | 10 | Very mild[d] | 0.3 (0.05–0.5) | 11 (9.6–17) |
| g5AV2⁻CP⁻ | 20 | Very mild[d] | 0.6 (0.1–2.7) | 15.2 (6.2–49.2) |
| g5⁻AV2⁻CP⁻ | 20 | Very mild[d] | 0.1 (0.0–0.2) | 5.7 (0.0–11.4) |
| CP⁻ | 20 | Severe[e] | 4.3 (2.6–6.5) | 102 (65–139) |
| CP66:g5 | 20 | mild | 2.2 (0.8–4.2) | 30.6 (15.3–55.1) |
| CP66:6G:g5 | 30 | Very mild[d] | 0.9 (0.4–1.7) | 10.9 (5.5–14.7) |
| cP66:g5⁻ | 20 | Severe[e] | 4.0 (1.8–6.1) | 139.7 (56.0–197.7) |

[a]The values represent the average amount (range) of single-stranded (ss) and double-stranded (ds) A component DNA in five independent protoplast transfections per mutant. Protoplasts (~10⁶) were transfected with 2 μg of A component DNA and 40 μg of herring sperm DNA. Viral DNA was quantitated on Southern blots using the "phosphorImager" from Molecular Dynamics.
[b]The values are average (range) amounts of viral DNA in twelve inoculated plants per virus construct except for AV2⁻CP⁻for which the values are averages of four plants. Each plant was inoculated with 0.5 μg of A and 0.5 μg of wild type B component DNA, which is essential for viral movement and symptom development.
[c]The amount of viral DNA in protoplasts and plants inoculated with the wild type viral DNA were assigned a value of 100.
[d]Many plants did not show symptoms.
[e]Severe symptoms like in plants inoculated with the wild type virus but without intense chlorosis.

Figure 3A:
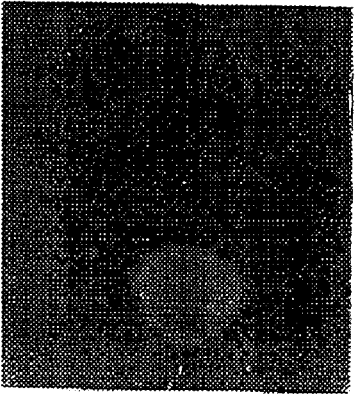
(FIG. 3A) Protoplast infected with CP66:Stag:6G:g5 virus and stained with S-protein coupled to FITC.
Figure 3B:
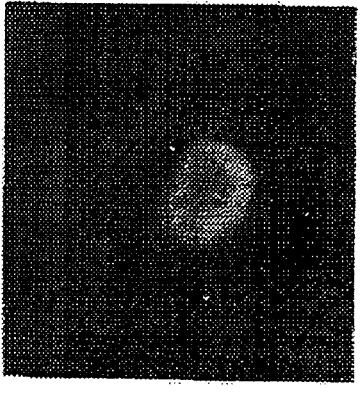
(FIG. 3B) Protoplast infected with wild type virus and stained with anti-CP antisera.
Figure 3C:
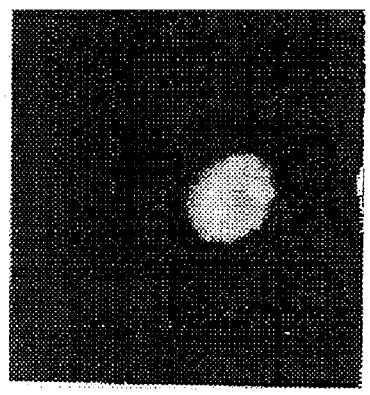
(FIG. 3C) Protoplast infected with CP66:GUS virus and stained with anti-GUS antisera.
Figure 3D:
(FIG. 3D) Protoplast infected with g5:GUSAV2$^-$CP$^-$ virus and stained with anti-GUS antisera.
Figure 3E:
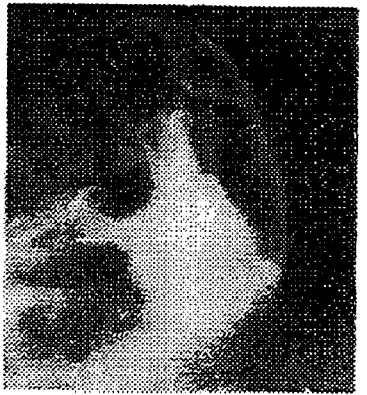
(FIG. 3E) Protoplast infected with GUSAV2$^-$CP$^-$ virus and stained with anti-GUS antisera.

Geminiviruses replicate in the nucleus (Accotto et al, *Virology*, 195:257–259, 1993; Nagar et al, *Plant Cell*, 7:705–719, 1995), so it is likely that in order to cause the accumulation of ssDNA the CP66:6G:g5 and g5 proteins must be present in the nucleus. To immunolocalize the CP66:6G:g5 fusion protein in protoplasts, the Stag epitope was inserted between Arg66 of the CP and the glycine linker (CP66:Stag:6G:g5, Table 1). At 48 h after infection protoplasts were fixed and subjected to reactions with S-protein coupled to FITC. The CP66:Stag:6G:g5 protein as well as the wt CP (detected with anti-CP antisera) were localized to the nucleus (FIGS. 3A and 3B). When GUS protein was produced as a fusion protein with the N-terminal 66 aa of CP (CP66:GUS), the GUS (detected with anti-GUS antisera) was also localized to the nucleus (FIG. 3C). This indicated that the N-terminal 66 aa of the CP contained a nuclear localization signal.

g5p contains a nuclear localization signal as shown by fusing g5 sequence to the sequence coding for GUS at the N-terminus. The g5:GUS fusion protein (expressed in g5:GUSAV2⁻CP⁻ virus A component, Table 1) and unfused GUS protein (expressed in GUSAV2⁻CP⁻virus A component, Table 1) remained in the cytoplasm (FIGS. 3D and 3E), indicating that g5p has no nuclear localization signal. The g5p most likely entered the nucleus in a passive manner based on its size (9.7 kDa) which is smaller than the permeability barrier of the nuclear envelop (Dingwall et al, *Ann. Rev. Cell Biol.*, 2:367–390, 1986).

7. Movement of ToLCV Expressing CP66:6G:g5 Protein is Impaired in Plants *N. benthamiana* plants were inoculated with selected virus constructs to determine the effect of g5p on virus spread: in these studies B component DNA was coinoculated with A component onto *N. benthamiana* seedlings. As expected, plants inoculated with A component mutants AV2⁻CP⁻, g5AV2⁻CP⁻, or g5⁻AV2⁻CP⁻ plus B component showed very mild or no symptoms and all inoculated plants accumulated low levels of viral DNA (Table 2). A previously reported ToCLV mutant (Padidam et al, *Virology*, 224:390–404, 1996) that did not produce CP but produced AV2 (CP⁻) developed severe disease symptoms and wt levels of dsDNA on systemic infections (Table 2). Surprisingly, plants inoculated with the virus expressing CP66:6G:g5 protein showed very mild or no symptoms even though the virus contained an intact AV2 gene (Table 2). These plants accumulated low levels of viral DNA similar to plants inoculated with AV2⁻CP⁻virus (Table 2). Plants inoculated with the virus expressing CP66:g5 protein (which accumulated ssDNA to a lower level than CP66:6G:g5 virus in protoplasts) showed mild symptoms and accumulated moderate levels of dsDNA. The impaired movement of the virus expressing g5p was due to possible toxic effects of g5p. No differences in protoplast viability or in appearance of plant leaves inoculated with wt virus or virus expressing g5p were detected that might suggest toxicity of g5p.

Figure 3F:
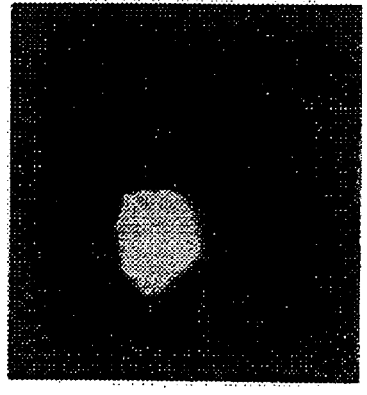
(FIG. 3F) Protoplast infected with FBV1AV2$^-$CP$^-$ virus and stained with anti-Flag antibody.
Figure 3G:
(FIG. 3G) Protoplasts infected with TBC1AV2$^-$CP$^-$ virus and stained with anti-T7 tag antibody. Note that two cells are shown in this micrograph. Inoculated leaf (FIG. 3H) and systemic leaf (FIG. 3I) of a plant infected with GFPAV2$^-$CP$^-$+CP66:g5$^-$ viruses 6 days post inoculation (dpi). Inoculated leaf (FIG. 3J) and systemic leaf (FIG. 3K) of a plant infected with GFPAV2$^-$CP$^-$+CP66:g5$^-$ viruses 15 dpi. Inoculated leaf (FIG. 3L) and systemic leaf (FIG. 3M) of a plant infected with GFPAV2$^-$CP$^-$+CP66:6G:g5 viruses 6 dpi. Inoculated leaf (FIG. 3N) and systemic leaves (FIGS. 3O and 3P) of a plant infected with GFPAV2$^-$CP$^-$+CP66:6G:g5 viruses 15 dpi.
Figure 3H:
FIG. 3 illustrates indirect immunofluorescence of proteins expressed in protoplasts (FIGS. 3A–3G) and fluorescence of green fluorescent protein (GFP) expressed in plants (FIGS. 3H–3P). Protoplasts were transfected and antigens were visualized with different antibodies and FITC- or rhodamine-conjugated secondary antibody. GFP fluorescence in plants was monitored every three days for 15 days and the area shown corresponds to 2.5×2.5 mm of leaf area.
Figure 3I:
Figure 3J:
Figure 3K:
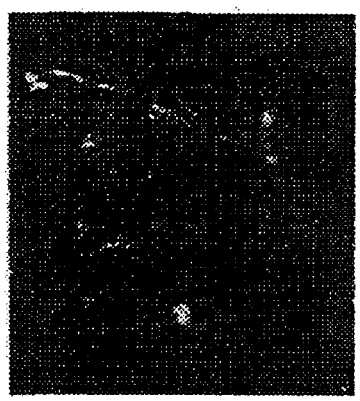
Figure 3L:
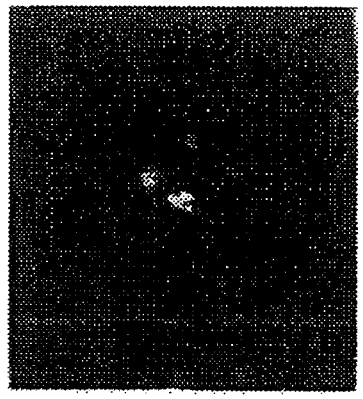
Figure 3M:
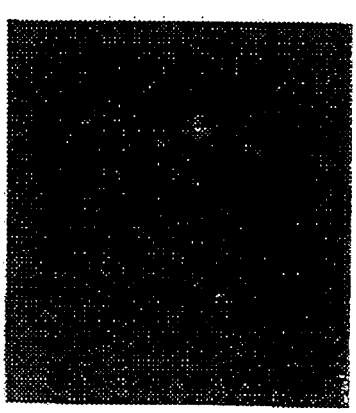
Figure 3N:
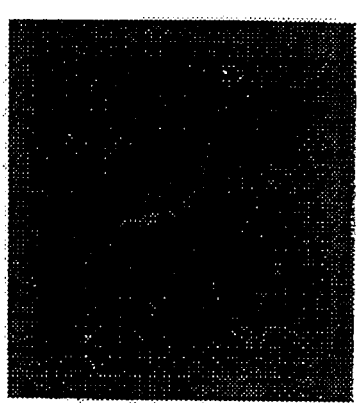
Figure 3O:
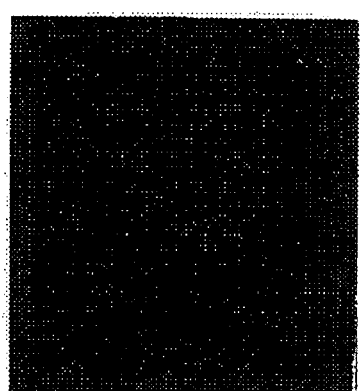
Figure 3P:
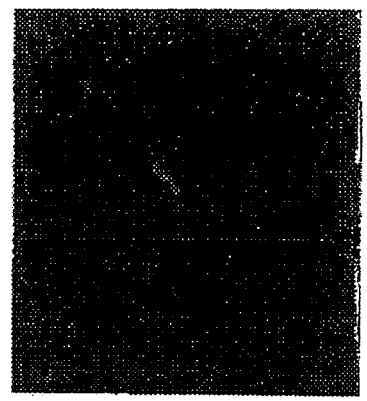

The cell to cell and long distance movement of ToLCV expressing CP66:6G:g5 protein was examined by utilizing green fluorescent protein (GFP) as a visible marker for virus movement. Plants were inoculated with A component DNA expressing GFP in place of AV2 and CP (GFPAV2⁻ᶜᴾ⁻) alone, or coinoculated with A component DNA of the wt, CP66:6G:g5, or CP66:g5⁻ construct. GFPAV2⁻CP⁻ virus was expected to move inefficiently in plants as it does not encode AV2; it was expected to move efficiently when complemented by another virus encoding AV2. GFP could not be detected in plants by 3 d post inoculation, but it was present on inoculated and upper leaves by day 6 in the majority of the plants inoculated with GFPAV2⁻CP⁻ plus wt A component, or GFPAV2⁻CP⁻ plus CP66:g5⁻viruses (FIG. 3H, 3I; only data on plants inoculated with GFPAV2⁻CP⁻ plus CP66:g5⁻ viruses is shown). The virus expressing GFP continued to spread to upper and newly emerging leaves in these plants (FIG. 3J, 3K). GFP was observed in veins, mesophyll and epidermal cells, and was present in large areas of the leaf in plants inoculated with GFPAV2–CP– plus CP66:g5– viruses. In contrast, GFP was restricted to small spots on the inoculated leaves of most of the plants inoculated with GFPAV2⁻CP⁻, or GFPAV2⁻CP⁻ plus CP66:6G:g5 viruses (FIG. 3L, 3M; only data on plants inoculated with GFPAV2⁻CP⁻ plus CP66:6G:g5 viruses is shown). These plants also showed GFP staining in some adjacent and newly emerging leaves, but mostly restricted to veins (FIG. 3N, 3O, 3P). These results indicated that expressing the g5p in place of CP has decreased the efficiency of the virus systemic movement.

8. In vivo Binding of CP66:6G:g5 Protein to Viral DNA

Figure 4A:
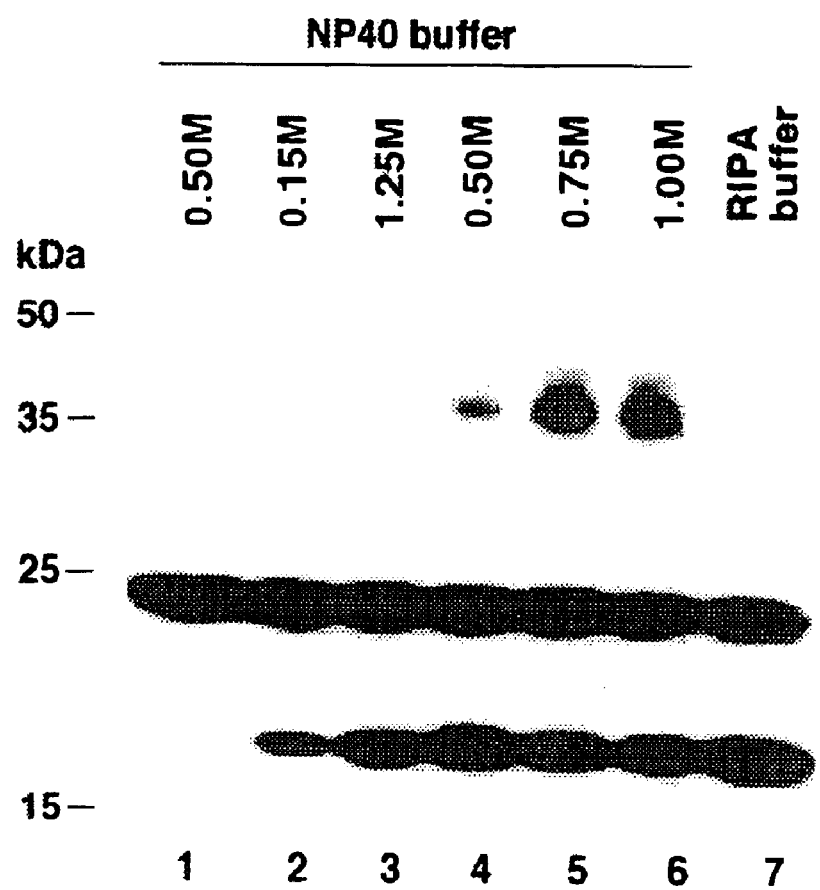
(FIG. 4A) Flag epitope-tagged CP66:6G:g5 protein expressed in protoplasts was immunoprecipitated with anti-Flag antibody coupled to agarose after lysing protoplasts in NP40 buffer containing different concentrations of NaCl (shown above the lanes) or RIPA buffer, and the immunoprecipitated protein was detected on a western blot with anti-Flag antibody (lanes 2–6). Lane 1 contained proteins immunoprecipitated from protoplasts transfected with wild type virus as a control. The protein band present in all lanes at ~24 kDa is the light chain of anti-Flag antibody used for immunoprecipitations. The immunoprecipitated CP66:6G:g5 protein was detected at two different molecular masses corresponding to monomer and dimer forms. Positions of molecular weight markers are indicated in kilodaltons on the left.
Figure 4B:
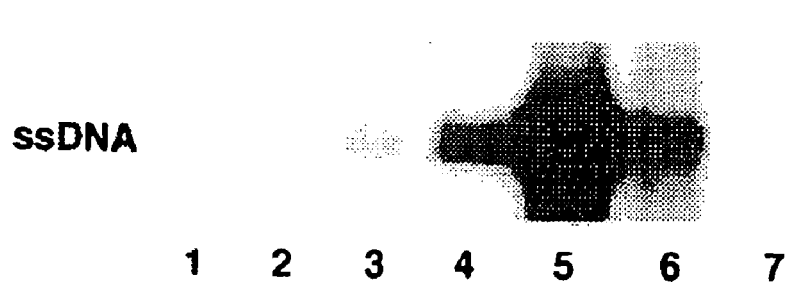
(FIG. 4B) Viral ssDNA that coimmunoprecipitated with the Flag epitope-tagged CP66:6G:g5 protein was detected on a Southern blot using 32P-labeled A component DNA as a probe. Lanes 1–7 have same treatments as shown in FIG. 4A.

The accumulation of viral sSDNA in protoplasts inoculated with virus A component expressing g5p or CP66:6G:g5 protein indicated that g5p binds to ssDNA. In verification, protoplasts were inoculated with virus A component expressing Flag epitope-tagged CP66:6G:g5 protein (FCP66:6G:g5, Table 1) and immunoprecipitated the Flag epitope-tagged CP66:6G:g5 protein using anti-Flag antibody and characterized the viral DNA that coimmunoprecipitated with the CP66:6G:g5 protein by Southern blotting. The immunoprecipitations were performed under different salt (1% NP40 buffer with 0.15 to 1.0 M NaCl) conditions and in the presence of 0.1 SDS, 0.5% DOC and 1% NP40 detergents (RIPA buffer) to assay the affinity of binding. Flag epitope-tagged CP66:6G:g5 protein was immunoprecipitated in all the buffer conditions tested; the amount of protein immunoprecipitated increased with the increase in salt concentration. (FIG. 4A). The amount of coimmunoprecipitated ssDNA increased up to 0.5 M salt and decreased at higher concentrations (FIG. 4B), indicating the g5p-ssDNA complex was destabilized in buffer that contained 1 M salt. Immunoprecipitation in RIPA buffer also resulted in reduced amount of precipitated DNA (FIG. 4B). These results showed that g5p bound to viral ssDNA and 1 M salt (in NP40 buffer) dissociated g5p from viral DNA.

9. Role of BV1 and BC1 Movement Proteins in Spread of ToLCV

Together, the above results indicate that CP66:6G:g5 protein is localized to the nucleus and binds stably to ToLCV virus DNA in vivo, and ToLCV expressing CP66:6G:g5 does not move efficiently in plants. The inefficient movement of ToLCV expressing CP66:6G:g5 protein may be due to interference of g5p with the function of BV1 or BC1 movement proteins of ToLCV. In squash leaf curl virus (SLCV), BV1 (referred to as BR1 in SLCV) protein, but not BC1 (referred to as BL1 in SLCV), binds to ssDNA in vitro (Pascal et al, *Plant Cell*, 6:995–1006, 1994) . BV1 and BC1 of SLCV interact with each other in a cooperative manner; in protoplasts BV1 localizes to the nucleus in the absence of BC1 but localizes to the cell periphery in the presence of BC1 (Sanderfoot et al, *Plant Physiol.*, 110:23–33, 1996; Sanderfoot et al, *Plant Cell*, 7:1185–1194, 1995). Both BV1 and BC1 are required for the systemic spread and symptom development of ToLCV (Padidam et al, *Virology*, 224:390–404, 1996). To determine if BV1 and BC1 of ToLCV have similar functions as BV1 and BC1 of SLCV, BV1 and BC1 of ToLCV were immunolocalized and examined for their ability to complement viral ssDNA accumulation of CP mutants. For these experiments BV1 and BC1 genes were fused to sequences coding for Flag epitope tag and T7 epitope tag, respectively, and inserted in place of AV2 and CP in the A component (FBV1AV2$^-$CP$^-$ and TBC1AV2$^-$CP$^-$, Table 1). In protoplasts inoculated with FBV1AV2$^-$CP$^-$ construct, BV1 protein accumulated in the nucleus (detected using anti-Flag antibody, FIG. 3F) while in protoplasts inoculated with TBC1AV2$^-$CP$^-$, the BC1 protein was localized to the cell periphery (detected using anti-T7 tag antibody, FIG. 3G) Expression of BV1 protein in place of AV2 and CP protein (BV1AV2$^-$CP$^-$) also led to the accumulation of ssDNA of the A component (Table 3; FIG. 2, lane 9). The binding affinity of BV1 protein tagged with Flag epitope to viral DNA in protoplasts inoculated with FBV1AV2$^-$CP$^-$ DNA was determined by immunoprecipitation reactions similar to those described in FIG. 4. The binding affinity of BV1 protein to viral ssDNA was similar to the binding affinity of CP66:6G:g5 protein to viral DNA. In contrast to results obtained with the A component DNA expressing BV1, A component DNA expressing BC1 protein in place of AV2 and CP (BC1AV2$^-$CP$^-$) did not accumulate ssDNA (Table 3; FIG. 2, lane 10). Since BC1 protein was localized to the cell periphery, BC1 was fused to N-terminal 66 aa of the CP (CP66:6G:BC1) to direct it to the nucleus. Virus A component DNA expressing the CP66:6G:BC1 protein also did not accumulate ssDNA (Table 3; FIG. 2, lane 11) showing that BC1 movement protein may not bind to viral ssDNA or the binding affinity was not sufficiently strong enough to result in the accumulation of ssDNA. These results show that BV1 is localized to the nucleus in the absence of BC1, and BV1 binds to viral ssDNA in vivo.

TABLE 3

Complementation by BV1 and BC1 movement proteins for the accumulation of tomato leaf curl virus ssDNA in protoplasts[a]

| A component | B component | ssDNA | dsDNA |
| --- | --- | --- | --- |
| Wild type | none | 100 | 100 |
| BV1AV2$^-$CP$^-$ | none | 86 (50–121) | 230 (119–195) |
| FB1AV2$^-$CP$^-$ | none | 33 (25–54) | 47 (40–58) |
| BC1AV2$^-$CP$^-$ | none | 2 (1–3) | 224 (162–288) |
| Cp66:6G:BC1 | none | 5 (1–10) | 214 (180–267) |
| Wild type | Wild type | 57 (37–78) | 61 (42–81) |
| Wild type | BC1$^-$ | 48 (38–58) | 50 (40–60) |
| AV2$^-$CP$^-$ | Wild type | 2.4 (1.2–3.6) | 131 (76–187) |
| AV2$^-$CP$^-$ | BC1$^-$ | 2.7 (1.5–4.0) | 135 (82–188) |
| CP$^-$ | Wild type | 2.5 (1.6–3.3) | 100 (78–121) |
| CP$^-$ | BC1$^-$ | 2.9 (2.1–3.7) | 106 (98–113) |

[a]Protoplasts were transfected with 2 μg of A component DNA with or without 10 μg of B component DNA. Viral single-stranded (ss) and double-stranded (ds) DNA was quantitated on Southern blots using "phoshorImager" and the values represent the average amount (range) of viral DNA in two to five independent transfections.

In plants inoculated with ToLCV A component containing CP66:6G:g5 gene plus wt B component the expression of CP66:6G:g5 protein is controlled by the relatively strong CP promoter. The CP66:6G:g5 protein produced from the A component may out-compete with the BV1 protein (expressed from the B component) for DNA binding if the amount of BV1 made under its own promoter is relatively low. We conducted an experiment to determine if BV1, expressed under its own promoter on the B component, can lead to accumulation of ssDNA. Note that BV1 led to accumulation of ssDNA when expressed in place of CP on A component (Table 3). However, very little viral ssDNA accumulated in protoplasts coinoculated with A component DNA with mutations in CP (CP$^-$) plus wt B component DNA (i.e., expressing both BV1 and BC1) or B component with a mutation in BC1 (BC1$^-$; i.e, expressing only BV1) (Table 3; FIG. 2, lanes 12–15). The failure of BV1 to cause accumulation of ssDNA when expressed from the B component appeared to be due to low levels of BV1 protein being made; no BV1 protein was detected in protoplasts coinoculated with A component DNA and B component DNA expressing Flag epitope-tagged BV1 by immunolocalization and western blotting procedures. These results show that the B component promoter driving the expression of BV1 is not as strong as when the gene was expressed from the CP promoter on the A component.

10. Discussion of Examples 1–9

A non-specific ssDNA binding protein (g5) was expressed in place of CP and was monitored for the accumulation of ssDNA to determine if it could serve as a substitute for CP in *Geminivirus*. The g5p from *E. coli* phage M13 was chosen because of its small size (9.7 kDa) and lack of any enzymatic function in DNA replication. The role of g5p in replication of M13 and other filamentous phages has been extensively studied (Rasched et al, *Microbiol. Rev.*, 50:401–427, 1986) and its structure has been determined (Skinner et al, *Proc. Natl. Acad. Sci. USA,* 91:2071–2075, 1994). Gene 5 protein binds newly formed viral ssDNA tightly, cooperatively, and in a sequence independent manner, and protects it from degradation by *E. coli* nucleases.

It is shown that g5p can bind to ToLCV ssDNA in plant cells and ToLCV expressing g5p or g5p fused to N-terminal 66 aa of the CP accumulated ssDNA to wt levels. The binding of g5p to viral ssDNA in vivo was similar to the binding of g5p to M13 ssDNA in vitro (Anderson et al, *Biochemistry*, 14:907–917, 1975). Though g5p compensated for the lack of CP by causing an increase in accumulation of ssDNA of ToLCV, it did not reduce the amount of dsDNA to wt levels. BV1 movement protein (when expressed in place of CP) also behaved like g5p in that it did not down-regulate the dsDNA to wt levels. If CP regulates the levels of ss and dsDNA by depleting the ssDNA available for conversion to dsDNA, expression of g5p or BV1 could be expected to result in normal amounts of dsDNA. The fact that it did not suggests that CP may have a direct role in regulating virus replication, possibly by inhibiting minus-strand synthesis or by regulating gene expression. The CP of alfalfa mosaic virus (A1MV), a virus with a ssRNA(+) genome, has been shown to play a direct role in regulation of plus- and minus-strand RNA synthesis. The A1MV CP was found in tight association with the viral RNA polymerase and inhibited minus-strand synthesis while stimulating plus-strand synthesis. Recent results on SLCV suggests that CP acts to signal the switch from viral dsDNA replication to ssDNA replication, or to sequester virion ssDNA from replication pool without fully encapsidating it. Purification of geminivirus replication complexes is needed to directly assess the role of CP in replication.

Plants infected with virus that encodes CP66:6G:g5 protein show very mild symptoms and accumulate low levels of viral DNA when infected protoplasts accumulated high levels of viral DNA. This occurs because by binding to viral ssDNA, g5p affects virus movement by interfering with the function of BV1 movement protein. BV1 of ToLCV was localized to the nucleus in infected protoplasts and bound to viral ssDNA in vivo; whereas BC1 was localized to the cell periphery and did not complement viral ssDNA accumulation even when it was directed to the nucleus as a fusion to the nuclear localizing signal of CP. Recent studies on the role of BV1 and BC1 in SLCV movement have shown that BV1 localizes to the nucleus, binds to ssDNA in vitro, and functions as a nuclear shuttle protein. BC1 of SLCV is localized to the cell periphery in protoplasts and is associated with endoplasmic reticulum-derived tubules in developing phloem cells of systemically infected pumpkin seedlings. Based on these results, a model for SLCV was proposed in which BC1 containing tubules serve as a conduit for the transport of BV1, and its associated viral ssDNA, from one cell to another (Ward et al, *J. Virol.*, 71:3726–33, 1997). Studies on TGMV have shown that BV1 interacts with viral ssDNA in vivo and BV1 and BC1 have distinct and essential roles in cell to cell movement as well as systemic movement (Jeffrey et al, *Virology.*, 223:208–218, 1996). ToLCV employs a similar strategy in moving from cell to cell. The poor movement of ToLCV that produces CP66:6g:g5 protein is due to reduced binding of BV1 to viral ssDNA. It should be noted that BV1 did not lead to accumulation of ssDNA of A component that lacked CP when BV1 was expressed under its own promoter from the B component. In plants coinoculated with A component producing CP66:6G:g5 plus A component producing GFP, GFP staining was mostly restricted to small areas, both on inoculated and systemically infected leaves, showing an over all reduction in the efficiency of viral movement than specific interference with cell to cell spread or long distance movement.

The interference with the ToLCV movement due to binding of g5p to viral ssDNA indicates that in this virus ssDNA moves from cell to cell. These results also indicate that expression of g5p in transgenic plants provides a novel way of controlling geminiviruses and that such resistance is effective against all geminiviruses.

In summary, to determine whether the gene 5 protein (g5p), a ssDNA binding protein from *Escherichia coli* phage M13, could restore the accumulation of ssDNA, ToLCV that lacked the CP gene was modified to express g5p or g5p fused to the N-terminal 66 amino acids of the CP (CP66:6G:g5). The modified viruses led to accumulation of wild type levels of ssDNA and high levels of dsDNA. The accumulation of ssDNA was due to stable binding of g5p to the viral ssDNA. The high levels of dsDNA accumulation during infections of the modified viruses indicated suggested a direct role for CP in viral DNA replication. ToLCV that produced CP66:6G:g5 protein did not spread efficiently in *Nicotiana benthamiana* plants and inoculated plants developed only very mild symptoms. In infected protoplasts CP66:6G:g5 protein was immunolocalized to nuclei; this indicates that the fusion protein interferes with the function of BV1 movement protein and thereby prevents spread of the infection.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A method for producing in a plant resistance to a single stranded DNA (ssDNA) virus of the *Geminivirus* family comprising introducing a gene 5 ssDNA-binding protein of Coliphage M13 into said plant, thereby producing resistance to said ssDNA virus in said plant.

2. The method of claim 1 wherein said Coliphage M13 gene 5 protein has the amino acid residue sequence of SEQ ID NO 1.

3. The method of claim 1 wherein said introducing comprises preparing a transgenic plant containing a gene which expresses said ssDNA-binding protein.

4. The method of claim 3 wherein said gene comprises a nucleotide sequence shown in SEQ ID NOs 2 or 3.

5. The method of claim 1 wherein said introducing comprises contacting said plant with a composition containing an expression vector capable of expressing said ssDNA-binding protein.

6. The method of claim 5 wherein said expression vector comprises a nucleotide sequence shown in SEQ ID NOs 2 or 3.

7. The method of claim 5 wherein said contacting comprises biolistic gene transfer or direct DNA uptake into protoplast.

8. The method of claim 5 wherein said contacting comprises infection of said plant with a carrier vector.

9. The method of claim 8 wherein said carrier vector is an *Agrobacterium* vector.

10. The method of claim 5 wherein said expression vector is present in a virus particle that infects said plant and expresses said ssDNA-binding coat protein.

11. The method of claim 1 wherein said plant is selected from the group consisting of *Abutilon, Acalypha*, apple, *Ageratum, Althea rosea, Asystasia*, Bajra, banana, barley, beans, beet, Blackgram, *Bromus*, Cassava, chickpea, Chilllies, *Chloris*, clover, coconut, coffee, cotton, cowpea, *Croton*, cucumber, *Digitaria, Dolichos*, eggplant, *Eupatorium, Euphorbia*, fababean, honeysuckle, horsegram, *Jatropha, Leonurus*, limabean, Lupin, *Macroptilium, Macrotyloma*, maize, melon, millet, mungbean, oat, okra, *Panicum, papaya, Paspalum*, peanut, pea, pepper, pigeon pea, pineapple, *Phaseolus*, potato, *Pseuderanthemum*, pumpkin, *Rhynchosia*, rice, Serrano, *Sida*, sorghum, soybean, squash, sugarcane, sugarbeet, sunflower, sweet potato, tea, tomato, tobacco, watermelon, wheat and *Wissadula*.

12. The method of claim 1 wherein said *Geminivirus* is selected from the group consisting of *Mastrevirus, Curtovirus* and *Begomovirus* genera.

13. A method for producing *geminivirus* resistance in a plant comprising introducing into said plant a gene capable of expressing Coliphage M13 gene 5 protein in said plant, thereby producing resistance to said geminivirus in said plant.

14. A DNA expression vector comprising a nucleotide sequence that encodes a gene 5 ssDNA-binding protein of Coliphage M13, wherein said vector is capable of expressing said protein in plants.

15. The DNA expression vector of claim 14 wherein said Coliphage M13 gene 5 protein has the amino acid residue sequence of SEQ ID NO 1.

16. The DNA expression vector of claim 14 wherein said nucleotide sequence comprises a nucleotide sequence shown in SEQ ID NOs 2 or 3.

17. The DNA expression vector of claim 14 wherein said vector is a carrier vector.

18. The DNA expression vector of claim 17 wherein said carrier vector is an *Agrobacterium* vector.

19. The DNA expression vector of claim 14 wherein said plant is selected from the group consisting of *Abutilon, Acalypha*, apple, *Ageratum, Althea rosea, Asystasia*, Bajra, banana, barley, beans, beet, Blackgram, *Bromus*, Cassava, chickpea, Chilllies, *Chloris*, clover, coconut, coffee, cotton, cowpea, *Croton*, cucumber, *Digitaria, Dolichos*, eggplant, *Eupatorium, Euphorbia*, fababean, honeysuckle, horsegram, *Jatropha, Leonurus*, limabean, Lupin, *Macroptilium, Macrotyloma*, maize, melon, millet, mungbean, oat, okra, *Panicum*, papaya, *Paspalum*, peanut, pea, pepper, pigeon pea, pineapple, *Phaseolus*, potato, *Pseuderanthemum*, pumpkin, *Rhynchosia*, rice, Serrano, *Sida*, sorghum, soybean, squash, sugarcane, sugarbeet, sunflower, sweet potato, tea, tomato, tobacco, watermelon, wheat and *Wissadula*.

20. A composition for producing resistance to a ssDNA virus of the *Geminivirus* family that infects plants comprising a DNA expression vector comprising a nucleotide sequence that encodes a gene 5 ssDNA-binding protein of Coliphage M13, wherein said vector expresses said protein in said plant.

21. The composition of claim 20 wherein said Coliphage M13 gene 5 protein has the amino acid residue sequence of SEQ ID NO 1.

22. The composition of claim 20 wherein said nucleotide sequence comprises a nucleotide sequence shown in SEQ ID NOs 2 or 3.

23. The composition of claim 20 wherein said DNA expression vector is a carrier vector.

24. The composition of claim 23 wherein said carrier vector is an *Agrobacterium* vector.

25. A transgenic plant containing a DNA expression vector comprising a nucleotide sequence that encodes a gene 5 ssDNA-binding protein of Coliphage M13, wherein said vector expresses said protein in said plant.

26. The transgenic plant of claim 25 wherein said DNA expression vector is the vector of claim 14.

27. The transgenic plant of claim 25 wherein said Coliphage M13 gene 5 protein has the amino acid residue sequence of SEQ ID NO 1.

28. The transgenic plant of claim 25 wherein said nucleotide sequence comprises a nucleotide sequence shown in SEQ ID NOs 2 or 3.

* * * * *

SEQUENCE LISTING

<160> NUMBER OF SEQ ID NOS: 9

<210> SEQ ID NO 1
<211> LENGTH: 87
<212> TYPE: PRT
<213> ORGANISM: Inovirus coliphage M13

<400> SEQUENCE: 1

Met Ile Lys Val Glu Ile Lys Pro Ser Gln Ala Gln Phe Thr Thr Arg
1               5                   10                  15

Ser Gly Val Ser Arg Gln Gly Lys Pro Tyr Ser Leu Asn Glu Gln Leu
            20                  25                  30

Cys Tyr Val Asp Leu Gly Asn Glu Tyr Pro Val Leu Val Lys Ile Thr
        35                  40                  45

```
Leu Asp Glu Gly Gln Pro Ala Tyr Ala Pro Gly Leu Tyr Thr Val His
    50                  55                  60

Leu Ser Ser Phe Lys Val Gly Gln Phe Gly Ser Leu Met Ile Asp Arg
65                  70                  75                  80

Leu Arg Leu Val Pro Ala Lys
                85

<210> SEQ ID NO 2
<211> LENGTH: 264
<212> TYPE: DNA
<213> ORGANISM: Inovirus coliphage M13

<400> SEQUENCE: 2
atgattaaag ttgaaattaa accatctcaa gcccaattta ctactcgttc tggtgtttct    60
cgtcagggca agccttattc actgaatgag cagctttgtt acgttgattt gggtaatgaa   120
tatccggttc ttgtcaagat tactcttgat gaaggtcagc cagcctatgc gcctggtctg   180
tacaccgttc atctgtcctc tttcaaagtt ggtcagttcg gttcccttat gattgaccgt   240
ctgcgcctcg ttccggctaa gtaa                                          264

<210> SEQ ID NO 3
<211> LENGTH: 264
<212> TYPE: DNA
<213> ORGANISM: Artificial Sequence
<220> FEATURE:
<223> OTHER INFORMATION: Synthetic

<400> SEQUENCE: 3
atgatcaagg tggagatcaa gcccagccag gcccagttca ccacccgcag cggcgtgagc    60
cgccagggca agccctacag cctgaacgag cagctgtgct acgtggacct gggcaacgag   120
taccccgtgc tggtgaagat cacccctggac gagggccagc ccgcctacgc ccccggcctg   180
tacaccgtgc acctgagcag cttcaaggtc ggccagttcg gcagcctgat gatcgaccgc   240
ctgcgcctgg tgcccgccaa gtaa                                          264

<210> SEQ ID NO 4
<211> LENGTH: 2739
<212> TYPE: DNA
<213> ORGANISM: Begomovirus tomato leaf curl virus

<400> SEQUENCE: 4
taatattacc gaatggccgc gcaaattttt aggtgggccc tcaaccaatg aaattcacgc    60
tacatggcct atttagtgcg tggggatcaa taaatagact tgctcaccaa gtttggatcc   120
acaaacatgt gggatccatt attgcacgaa tttcccgaaa gcgttcatgg tctaaggtgc   180
atgctagctg taaatatctc caagagataa gaaagaact attcaccaga cacagtcggc   240
tacgatctta ttcgagatct cattcttgtt ctccgagcaa agaactatgg cgaagcgacc   300
agcagatatc atcatttcaa cgcccgcatc gaaggtacgc cgacgtctca acttcgacag   360
cccctatgga gctcgtgcag ttgtccccat gcccgcgtc accaaagcaa aggcctggac   420
caacaggccg atgaacagaa acccagaat gtacagaatg tatagaagtc ccgacgtgcc   480 aagggggctgt gaaggccctt gtaaagtgca gtcctttgaa tctaggcacg atgtctctca   540
tattggcaaa gtcatgtgtg ttagtgatgt tacccgagga actggactca cacatcgcgt   600
agggaagcga ttctgtgtga aatctgtcta tgtgctggga agatatgga tggatgaaaa   660 catcaagaca aaaaaccata ctaacagtgt catgttttt ctggttcgtg accgtcgtcc   720
```

```
tacaggatct cccaggatt tcggggaagt gtttaatatg tttgacaatg aaccgagcac    780
agcaacggtg aagaacatgc atcgtgatcg ttatcaagtc ttacggaagt ggcatgcgac    840
tgtgacggga ggaacatatg catctaagga gcaagcatta gttaggaagt tgttagggt     900
taataattat gttgtttata atcaacaaga ggccggcaag tatgagaatc atactgaaaa   960
cgcattaatg ttgtatatgg cctgtactca cgcatcaaat cctgtatatg ctactttgaa   1020
aatccggatc tacttttatg attcggccac aaattaataa atatccagtt ttatatcata   1080
cgaagtccat acatcaattg tttgctccaa tacattatcc aatacatgat aaactgctct   1140
tattacatta taaattccta tgacacctaa catatccagg tacttaagga cctgggtttt   1200
gaagactctc aagaaaatcc caatctgagg gcgtaagccc gtccagattt tgaaagttag   1260
aaaacacttg tgaagtccca gggctttccg caggttgtgg ttgaactgta tttgaatctt   1320
gattatgtcg tgctgtgtta ggaagggcct gctgtcgtgt ttcaaaattt tgaaatacag   1380
gggatttcga atttcccagg tatatacgcc actctctgct cgatccgcag tgatgtattc   1440
ccctgtgcgt gaatccgtga tcatggcagt tgatcgatat gtaatacgaa caaccacacg   1500
gtagatcaac tcgcctcctg cgaatgctct tcttcttctt ctgggagagc gatgttttcg   1560
cgaccggaat agagtggttc ttcgagtgtg atgaagactg cattcttgat tgcccactgc   1620
ttcagtgctg cattttttc ttcatccaga tattccttat agctgctgtt tggaccttta   1680
ttgcacagga agatagtggg aattccacct ttaatcatga ccggctttcc gtacttcgtg   1740
ttgctttggc agtcacgctg ggcccccatg aattctttaa agtgctttag atagtgggga   1800
tcaacgtcat caatgacgtt gtaccaggca tcattgctat agacctttgg gctcagatca   1860
agatgtccac acaagtaatt gtgtggtcct aagcaccgag cccacatcgt tttgcccgtc   1920
ctactatccc cctctatgac tatgcttatg ggcctaaaag gccgcgcagc ggcacacaca   1980
acattagacg agacccaatc gacgaggtct gccggaactc tgtcgaagga tgaaattgaa   2040
aatggagaaa cataaacctc ggaaggaggt tgaaaaatac gatctaaatt ggtatttaaa   2100
ttgtgaaact gcagaacgta atcttttggg gctaattcct ttaatactct caaagcatcg   2160
tctttatttc ccgtgttaat cgcctgggca tatgcatcgt tcgccgtttg ttgaccacca   2220
cgggcagatc gtccatcgat ctggaaaaca ccccattcta gaacgtctcc atctttggcg   2280
atgtagtttt tgacgtccga cgctgattta gctccctgaa tgttcggatg gaaatgtgct   2340
gaccgacttg gggaaaccaa gtcgaagaat ctgttatttt tgcactggaa tttcccttcg   2400
aattggatga aacatggat atgcggagac ccatcttcgt gaagctctct acagatcttg   2460
atgaatttct tcttcgtcgg ggtttctagg gtttgcaatt gggagagtgc ctcttctttta   2520
gttagagagc actttggata tgtgaggaaa tagttttttgg catttactct aaaacgacgt   2580
ggcgaagcca taaacttgt cgttttgatt cggcgtccct caactatct atatgattgg     2640
tgtctggagt cctatatata ggtaagacac catatggcat tattgtaatt ttgaaaagaa    2700
aattacttta attcaaattc cctaaagcgg ccattcgta                          2739
```

<210> SEQ ID NO 5
<211> LENGTH: 2696
<212> TYPE: DNA
<213> ORGANISM: Begomovirus tomato leaf curl virus
<400> SEQUENCE: 5

```
taatattacc gaaaggccgc gaaaattttg acccccttat cctgaccgtt gatgcgtaat    60
```

-continued

```
cattgcacgc cgttatccgt ccgatttgca acacgtgtat cccactaaca gactttatgg    120
aaaataaatg tgtgaatgcg tctctttct gcatatgtgt tccccatatg tctttatcgt    180
acttctatta tatgcgtctg tggtccccccc gcattatata aagtctttca cataaatcaa    240
attgccttct ttgctatgta tattttgatc ggtcgagatc aaaattaata tgttgcgaac    300
atatccgtcg ttcgatctta tgagatatgc tttaattcaa acaatacttg tttgaatttt    360
atgcacgctg tacaatacta gtttataaaa ctgctacata tgtgacatta catggtgttt    420
ccgttgccac acatttccta tcccagccaa atggcgtttc cctctcctta ttccacgcct    480
cgtcgttcgg gttacccatt caacagaaca tacaacggaa acaagagttt ccgcttgtgg    540
aagacccgga agtatcaaaa ctggaagcgc tatcgcagta cccattccat agcacgttct    600
ccaaccgaac tgtttggcga tccaatctcc aaacaatata cgcgtaagga aatctgtgaa    660
acacaggagg gttcggagta tctgctgcac aacaatcgtt acatgacgtc atatgtcacg    720
tatccatcaa aaacaagaac tggaacggac aaccgcgttc gttcctatat caagctaaag    780
agtctgaaca tatctgggac atttgctgtt cgtaaatctg acttgatgac cgaagtggtg    840
caaacaaatg gtctatacgg agtgatgtct atagttgtag tccgcgataa atctccaaag    900
atttattctg cgacccaacc tttaataccg tttgttgagc tatttggatc tgttaatgct    960
tgcaggggca gtctgaaagt ggcagaacgc caccatgaac gcttcgtact tctgaatcaa   1020
acatccatcg ttgtcaatac cccacattcc aacgctatca agaaattctg cattcgtaac   1080
tgcatcccaa gaacttacac aacctgggta acgttcaagg acgaagaaga agatagctgt   1140
actggacgat attctaacac cctccgaaat gcaattattt tatattatgt atggttaagc   1200
gatgtatcct cacaagtcga tctttacagc aatgtaattc ttaattacat tggataatat   1260
ataaaaatgc agaagaaaca tcttattttt tgaataaatt tggcttaaaa tttattacac   1320
gctcttcgat actggagcat ttacattgga ttttatacat tgctctacag tcttccgtaa   1380
ttatatctgc aatctcttcc cttgtaatac tccccgcctg tgatgccgat ggacctggat   1440
caattgccga atcatccaat ccgctcagat ttttatatgg tctgctggtg acggacgaaa   1500
gtccgatctc cgatctgctt gcccatgatt cgttcggacc tatagccaga tagggtaccc   1560
gtaacgatct tgaactatgt cccattaacc ttgaaccatc tacaagacgc cttgtttgtg   1620
gtttggaacc cacagaccag aaatcaatgt cgttcatagt gaattccttg gtctgtattt   1680
ctatctttgg tggtcggaat tcgacgtcag tcgaatgttt agccgacgac agcttcaatt   1740
tccctagcat cttacagaag tgtaccccat tcacgacgtt tgtgttctcc actcggtatt   1800
caactctcca aggattctta tccttgagag agaagaatga ggaagagtag tagtgcaggt   1860
tgcaattgca tttgatcgga attgtgaatt ccgcttgttt tgtgtccccc tccgtcaatc   1920
tcatgtcgtg tatctctacc acgacatgac caacagcatt aattggaacc tgactgcgat   1980
attccagaac tacgtgatct attttcatgc atctattcct caactggcta agcttctgct   2040
cgaacatgga tggaaatgac aaggtaactt ctgcagcatc gtttgtgaga gcgtactcaa   2100
cgcgctcaga ttgaatatac ccacctactc ccatacccat accatcattt cctattgaca   2160
tattggccgc gcagcgcaaa acccactgaa acacagaagg acagactacg atcaaagaaa   2220
ccccgacgaa gaagaaaccc tagcaaacaa cgaagttgtt ttgcaaagaa cggatgtaga   2280
tggttttata atgctattgc atgtcatgtc tatgtcatac caattaccct aaaatgaacg   2340
gcacatattt ttctacgaaa aaggagttgt gcatgcatat gggatgtctg tttatttacg   2400
gtataaattg gaagcccaat ttatttaatt gggctgaagt ttaaattcag aagaagtcca   2460
```

-continued

| | |
|---|---|
| tgaaattggc ccagcatcca ggtccattgt taaaatgaca tcgtttgtgt gttattgtgt | 2520 |
| gtatagaagt tagagagaag cagcagtttc tctctctaga actcatcggg tgtctctcaa | 2580 |
| cttatctata taattggtgt ctggagtcct atatataggt aagacaccat atggcattat | 2640 |
| tgtaattgtg aaagaaaat tactttaatt caaattccct atagcggcct ttcgta | 2696 |

<210> SEQ ID NO 6
<211> LENGTH: 2958
<212> TYPE: DNA
<213> ORGANISM: Unknown
<220> FEATURE:
<223> OTHER INFORMATION: pBluescript SK plasmid expression vector

<400> SEQUENCE: 6

| | |
|---|---|
| cacctgacgc gccctgtagc ggcgcattaa gcgcggcggg tgtggtggtt acgcgcagcg | 60 |
| tgaccgctac acttgccagc gccctagcgc ccgctccttt cgctttcttc ccttcctttc | 120 |
| tcgccacgtt cgccggcttt ccccgtcaag ctctaaatcg ggggctccct ttagggttcc | 180 |
| gatttagtgc tttacggcac ctcgacccca aaaaacttga ttaggtgat ggttcacgta | 240 |
| gtgggccatc gccctgatag acggttttc gcccttgac gttggagtcc acgttcttta | 300 |
| atagtggact cttgttccaa actggaacaa cactcaaccc tatctcggtc tattcttttg | 360 |
| atttataagg gattttgccg atttcggcct attggttaaa aaatgagctg atttaacaaa | 420 |
| aatttaacgc gaattttaac aaaatattaa cgcttacaat ttccattcgc cattcaggct | 480 |
| gcgcaactgt tgggaagggc gatcggtgcg ggcctcttcg ctattacgcc agctggcgaa | 540 |
| agggggatgt gctgcaaggc gattaagttg ggtaacgcca gggttttccc agtcacgacg | 600 |
| ttgtaaaacg acggccagtg aattgtaata cgactcacta tagggcgaat tgggtaccgg | 660 |
| gccccccctc gaggtcgacg gtatcgataa gcttgatatc gaattcctgc agcccggggg | 720 |
| atccactagt tctagagcgg ccgccaccgc ggtggagctc cagcttttgt tccctttagt | 780 |
| gagggttaat ttcgagcttg gcgtaatcat ggtcatagct gtttcctgtg tgaaattgtt | 840 |
| atccgctcac aattccacac aacatacgag ccggaagcat aaagtgtaaa gcctggggtg | 900 |
| cctaatgagt gagctaactc acattaattg cgttgcgctc actgcccgct ttccagtcgg | 960 |
| gaaacctgtc gtgccagctg cattaatgaa tcggccaacg cgcggggaga ggcggtttgc | 1020 |
| gtattgggcg ctcttccgct tcctcgctca ctgactcgct gcgctcggtc gttcggctgc | 1080 |
| ggcgagcggt atcagctcac tcaaaggcgg taatacggtt atccacagaa tcaggggata | 1140 |
| acgcaggaaa gaacatgtga gcaaaaggcc agcaaaaggc caggaaccgt aaaaaggccg | 1200 |
| cgttgctggc gtttttccat aggctccgcc cccctgacga gcatcacaaa aatcgacgct | 1260 |
| caagtcagag gtggcgaaac ccgacaggac tataaagata ccaggcgttt ccccctggaa | 1320 |
| gctccctcgt gcgctctcct gttccgaccc tgccgcttac cggatacctg tccgcctttc | 1380 |
| tcccttcggg aagcgtggcg ctttctcata gctcacgctg taggtatctc agttcggtgt | 1440 |
| aggtcgttcg ctccaagctg ggctgtgtgc acgaaccccc cgttcagccc gaccgctgcg | 1500 |
| ccttatccgg taactatcgt cttgagtcca acccggtaag acacgactta tcgccactgg | 1560 |
| cagcagccac tggtaacagg attagcagag cgaggtatgt aggcggtgct acagagttct | 1620 |
| tgaagtggtg gcctaactac ggctacacta aaggacagt atttggtatc tgcgctctgc | 1680 |
| tgaagccagt taccttcgga aaagagttg gtagctcttg atccggcaaa caaaccaccg | 1740 |
| ctggtagcgg tggttttttt gtttgcaagc agcagattac gcgcagaaaa aaaggatctc | 1800 |

```
aagaagatcc tttgatctttt tctacggggt ctgacgctca gtggaacgaa aactcacgtt    1860
aagggatttt ggtcatgaga ttatcaaaaa ggatcttcac ctagatcctt ttaaattaaa    1920
aatgaagttt taaatcaatc taaagtatat atgagtaaac ttggtctgac agttaccaat    1980
gcttaatcag tgaggcacct atctcagcga tctgtctatt tcgttcatcc atagttgcct    2040
gactccccgt cgtgtagata actacgatac gggagggctt accatctggc cccagtgctg    2100
caatgatacc gcgagaccca cgctcaccgg ctccagattt atcagcaata aaccagccag    2160
ccggaagggc cgagcgcaga agtggtcctg caactttatc cgcctccatc cagtctatta    2220
attgttgccg ggaagctaga gtaagtagtt cgccagttaa tagtttgcgc aacgttgttg    2280
ccattgctac aggcatcgtg gtgtcacgct cgtcgtttgg tatggcttca ttcagctccg    2340
gttcccaacg atcaaggcga gttacatgat cccccatgtt gtgcaaaaaa gcggttagct    2400
ccttcggtcc tccgatcgtt gtcagaagta agttggccgc agtgttatca ctcatggtta    2460
tggcagcact gcataattct cttactgtca tgccatccgt aagatgcttt tctgtgactg    2520
gtgagtactc aaccaagtca ttctgagaat agtgtatgcg gcgaccgagt tgctcttgcc    2580
cggcgtcaat acgggataat accgcgccac atagcagaac tttaaaagtg ctcatcattg    2640
gaaaacgttc ttcggggcga aaactctcaa ggatcttacc gctgttgaga tccagttcga    2700
tgtaacccac tcgtgcaccc aactgatctt cagcatcttt tactttcacc agcgtttctg    2760
ggtgagcaaa aacaggaagg caaaatgccg caaaaaaggg aataagggcg acacggaaat    2820
gttgaatact catactcttc ctttttcaat attattgaag catttatcag ggttattgtc    2880
tcatgagcgg atacatattt gaatgtattt agaaaaataa acaataggg gttccgcgca    2940 catttccccg aaaagtgc                                                  2958
```

<210> SEQ ID NO 7
<211> LENGTH: 15
<212> TYPE: PRT
<213> ORGANISM: Artificial Sequence
<220> FEATURE:
<223> OTHER INFORMATION: Synthesized

<400> SEQUENCE: 7

Lys Glu Thr Ala Ala Ala Lys Phe Glu Arg Gln His Met Asp Ser
 1               5                  10                  15

<210> SEQ ID NO 8
<211> LENGTH: 9
<212> TYPE: PRT
<213> ORGANISM: Artificial Sequence
<220> FEATURE:
<223> OTHER INFORMATION: Synthesized

<400> SEQUENCE: 8

Met Asp Tyr Lys Asp Asp Asp Asp Lys
 1               5

<210> SEQ ID NO 9
<211> LENGTH: 11
<212> TYPE: PRT
<213> ORGANISM: Artificial Sequence
<220> FEATURE:
<223> OTHER INFORMATION: Synthesized

<400> SEQUENCE: 9

Met Ala Ser Met Thr Gly Gly Gln Gln Met Gly
 1               5                  10